(12) United States Patent
Beer-Romero et al.

(10) Patent No.: US 7,566,455 B1
(45) Date of Patent: Jul. 28, 2009

(54) E6AP-BINDING PROTEINS

(75) Inventors: Peggy L. Beer-Romero, Arlington, MA (US); Giulio Draetta, Weymouth, MA (US); Mark Rolfe, Newton Upper Falls, MA (US)

(73) Assignee: GPC Biotech, Inc., Princeton, NJ (US)

( * ) Notice: Subject to any disclaimer, the term of this patent is extended or adjusted under 35 U.S.C. 154(b) by 0 days.

(21) Appl. No.: 08/484,878

(22) Filed: Jun. 7, 1995

(51) Int. Cl.
*A61K 39/00* (2006.01)

(52) U.S. Cl. .................................. 424/185.1

(58) Field of Classification Search ............ 514/2, 514/12; 530/350; 424/185.1, 192.1, 193.1; 435/69.7; 536/23.5
See application file for complete search history.

(56) References Cited

U.S. PATENT DOCUMENTS 5,457,189 A 10/1995 Crooke et al. ............. 536/24.5

OTHER PUBLICATIONS

Hillier et al. ya12e08.r3 *Homo sapiens* cDNA clone 61286 5' similar to SP:G10_XENLA P12805 G10. EST-STS Database Accession No. T39861, Feb. 22, 1995.*

Hla et al. Characterization of edg-2, a human homologue of the *Xenopus* maternal transcript G10 from endothelial cells. Biochimica et Biophysica Acta. vol. 1260, pp. 227-229, Jan. 25, 1995.*

McGrew et al. Poly(A) elongation during *Xenopus* oocyte maturation is required for translational recruitment and is mediated by a short sequence element. Genes & Development. vol. 3, pp. 803-815, 1989.*

Luban et al. The yeast two-hybrid system for studying protein-protein interactions. Current Opinion in Biotechnology. vol. 6, pp. 59-64, 1995.*

Mendelsohn et al. Applications of interaction traps/two-hybrid systems to biotechnology research. Current Opinions in Biotechnology. vol. 5, pp. 482-486, 1994.*

George et al., Macromolecular sequencing and synthesis, Anal Riss, p. 127-149, 1988.*

Ciechanover A. et al. (1994) "Degradation of the tumor suppressor protein p53 by the ubiquitin-mediated proteolytic system requires a novel species of ubiquitin-carrier protein, E2." *J Biol Chem* 269 (13):9582-9.

Freeman, S.M. et al. (1993) "Clinical trails in gene therapy." *Advanced Drug Delivery Reviews* 12:169-183.

Gutierrez, A.A. et al. (1992) "Gene therapy for cancer." *The Lancet* 339:715-721.

Huibregtse J.M. et al. (1991) "A cellular protein mediates association of p53 with the E6 oncoprotein of human papillomavirus types 16 or 18." *EMBO J* 10 (13): 4129-35.

Huibregtse, J.M. et al. (1993) "The interaction of the human papillomavirus E6 protein with p53." *Cancer Research Weekly* Aug. 23, 1993 [abstract cited].

Huibregtse J.M. et al. (1993) "Cloning and expression of the cDNA for E6-AP, a protein that mediates the interation of the human papillomavirus E6 oncoprotein with p53." *Mol Cell Biol* (2): 775-84.

Huibregtse J.M. et al. (1993) "Localization of the E6-AP regions that direct human papilloma-virus E6 binding, association with p53, and ubiquitination of associated proteins." *Mol Cell Biol* (8): 4918-27.

Huibregtse J.M. et al. (1995) "A family of proteins structurally and functionally related to the E6-AP ubiquitin-protein ligase." *Proc Natl Acad Sci USA* 92 (7): 2563-7.

Keen N. et al. (1994) "Interaction of the E6 protein of human papillomavirus with cellular proteins." *Oncogene* (5): 1493-9.

Molinari M. and Milner J. (1995) "p53 in complex with DNA is resistant to ubiquitin-dependent proteolysis in the presence of HPV-16 E6." *Oncogene* 10 (9):1849-54.

Rofle, M. et al. (1995) "Reconstitution of p53-ubiquitinylation reactions from purified components" *Proc. Natl. Acad. Sci. USA* 92:3264-3268.

Scheffner, M. et al. (1993) "The HVP-16 E6 and E6-AP complex functions as a ubiquitin-protein ligase in the ubiquitination of p53." *Cell* 75:495-505.

Scheffner M. et al. (1994) "Identification of a human ubiquitin-conjugating enzyme that mediates the E6-AP-dependent ubiquitination of p53." *Proc Natl Acad Sci USA* 91 (19): 8797-801.

Scheffner M. et al. (1995) "Protein ubiquntination involving an E1-E2-E3 enzyme ubiquitin thioester cascade." *Nature* 373 (6509):81-3.

* cited by examiner

*Primary Examiner*—Lorraine Spector
(74) *Attorney, Agent, or Firm*—Leon R. Yankwich; Yankwich & Associates, P.C.

(57) ABSTRACT

The present invention relates to the discovery in eukaryotic cells, particularly human cells, of novel protein-protein interactions between certain cellular proteins, referred to herein as "E6AP-binding proteins" or "E6AP-BPs", and the cellular protein E6AP, the latter of which is a component of a ubiquitin-ligase (E3) enzyme. The association of E6AP and the subject E6AP-binding proteins implicates the E6AP-binding proteins in a number of basic cellular functions, such as regulation of gene expression, regulation of the cell-cycle, modification of cell surface receptors, biogenesis of ribosomes, and DNA repair. One of the E6AP-binding proteins shares certain homology with the papillomavirus E6 protein, which also binds E6AP.

17 Claims, 3 Drawing Sheets

FIGURE 2A

```
E6     LFVVYRDSIPHAACHKCID-FYSR---IRELRHYS-DSVYGD--TLEKLTNTGLYNLLIRCLRC
       L.  ::R  I.H. :    :D-FY.R      REL :Y. . Y:D   ..K .: G Y: L  CLRC
cln57  LWPIFR--IHHQKTRYIFDLFYKRKAISRELYDYCIREGYADKNLIAKWKKQG-YENLC-CLRC
               50        60         70        80        90        100
                  60        70        80        90       100
```

E6AP-BINDING PROTEINS

BACKGROUND OF THE INVENTION

The ubiquitin-mediated proteolysis system is the major pathway for the selective, controlled degradation of intracellular proteins in eukaryotic cells. Ubiquitin modification of a variety of protein targets within the cell appears to be important in a number of basic cellular functions such as regulation of gene expression, regulation of the cell-cycle, modification of cell surface receptors, biogenesis of ribosomes, and DNA repair. One major function of the ubiquitin-mediated system is to control the half-lives of cellular proteins. The half-life of different proteins can range from a few minutes to several days, and can vary considerably depending on the cell-type, nutritional and environmental conditions, as well as the stage of the cell-cycle.

Targeted proteins undergoing selective degradation, presumably through the actions of a ubiquitin-dependent proteosome, are covalently tagged with ubiquitin through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and in some instances may also require auxiliary substrate recognition proteins (E3s). Following the linkage of the first ubiquitin chain, additional molecules of ubiquitin may be attached to lysine side chains of the previously conjugated moiety to form branched multi-ubiquitin chains.

The conjugation of ubiquitin to protein substrates is a multi-step process. In an initial ATP requiring step, a thioester is formed between the C-terminus of ubiquitin and an internal cysteine residue of an E1 enzyme. Activated ubiquitin is then transferred to a specific cysteine on one of several E2 enzymes. Finally, these E2 enzymes donate ubiquitin to protein substrates. Substrates are recognized either directly by ubiquitin-conjugated enzymes or by associated substrate recognition proteins, the E3 proteins, also known as ubiquitin ligases.

Ubiquitin is itself a substrate for ubiquitination. Depending on the ubiquitin-conjugating enzyme and the nature of the substrate, specific lysine residues of ubiquitin are used as acceptor sites for further ubiquitinations. This can lead to either a linear multi-ubiquitin chain (when a single lysine residue of ubiquitin is used) or multi-ubiquitin "trees" (when more than one lysine reside of ubiquitin is used). Although the attachment of a single ubiquitin moiety to a substrate can be sufficient for degradation, multi-ubiquitination appears to be required in most cases.

Many proteins that control cell-cycle progression are short-lived. For example, regulation of oncoproteins and anti-oncoproteins clearly plays an important role in determining steady-state levels of protein expression, and alterations in protein degradation are as likely as changes in transcription and/or translation to cause either the proliferative arrest of cells, or alternatively, the transformation of cells.

For instance, the p53 protein is a key regulator of mammalian cell growth and its gene is frequently mutated in a wide range of human tumors (Hollstein et al. (1991) *Science* 253: 49-53). Furthermore, many DNA tumor viruses encode viral antigens that inactivate p53 (e.g., see Vogelstein et al. (1992) *Cell* 70:523-526). The high risk human papillomaviruses, such as HPV-16 and -18, are strongly implicated in the pathogenesis of cervical carcinoma (zur Hansen et al. (1991) *Science* 254:1167-1173). These viruses encode two transforming proteins, E6 and E7, that target the cellular growth regulators p53 and pRb respectively. The mode of inactivation of p53 by E6 is apparently mediated by a ubiquitin-dependent pathway. Viral E6 and a cellular E6-associated protein (E6AP) combine to stimulate the ubiquitination of p53, thus targeting p53 for degradation (Scheffner et al. (1990) *Cell* 63:1129-1136. In this reaction, E6 and E6AP are thought to be providing a ubiquitin ligase, or E3-like activity (Scheffner et al. (1993) *Cell* 75:495-505).

SUMMARY OF THE INVENTION

The present invention relates to the discovery in eukaryotic cells, particularly human cells, of novel protein-protein interactions between the cellular protein E6AP and certain other cellular proteins, referred to hereinafter as "E6AP-binding proteins" or "E6AP-BP".

In one aspect, the invention features an E6AP-binding protein referred to herein as "cln57". In preferred embodiments, the invention provides a substantially pure preparation of an cln57 polypeptide, or a recombinant cln57 polypeptide. In preferred embodiments the polypeptide has a biological activity associated with its binding to E6AP, e.g., it retains the ability to bind to an E6AP protein, though it may be able to either agonize or antagonize assembly of E6AP-containing protein complexes. The polypeptide can be identical to the cln57 polypeptide shown in SEQ ID No:5, or it can merely be homologous to that sequence. For instance, the cln57 polypeptide preferably has an amino acid sequence at least 60% homologous to the amino acid sequence in SEQ ID No:5, though higher sequence homologies of, for example, 80%, 90% or 95% are also contemplated. The cln57 polypeptide can comprise the full length protein represented in SEQ ID No:5, or it can comprise a fragment of that protein, which fragment may be, for instance, at least 5, 10, 20, 50 or 100 amino acids in length. As described below, the cln57 polypeptide can be either an agonist (e.g. mimics), or alternatively, an antagonist of a biological activity of a naturally occurring form of the cln57 protein, e.g., the cln57 polypeptide is able to modulate E6AP-mediated regulation of cell cycle, differentiation and survival In a preferred embodiment, a peptide having at least one biological activity of the subject cln57 polypeptide may differ in amino acid sequence from the sequence in SEQ ID No:5, but such differences result in a modified protein which functions in the same or similar manner as the native E6AP-binding protein or which has the same or similar characteristics of the native E6AP-binding protein. However, homologs of the naturally occurring cln57 protein are contemplated which are antagonistic of the normal cellular role of the naturally occurring cln57 protein. For example, the homolog may be capable of interfering with the ability of E6AP to modulate gene degradation of cell cycle regulatory proteins, e.g., p53.

In yet other preferred embodiments, the E6AP-binding protein is a recombinant fusion protein which includes a second polypeptide portion, e.g., a second polypeptide having an amino acid sequence unrelated to cln57, e.g. the second polypeptide portion is glutathione-S-transferase, e.g. the second polypeptide portion is a DNA binding domain of transcriptional regulatory protein, e.g. the second polypeptide portion is an RNA polymerase activating domain, e.g. the fusion protein is functional in a two-hybrid assay.

Yet another aspect of the present invention concerns an immunogen comprising an cln57 peptide in an immunogenic preparation, the immunogen being capable of eliciting an immune response specific for said E6AP-BP polypeptide; e.g. a humoral response, e.g. an antibody response; e.g. a cellular response. In preferred embodiments, the immunogen comprising an antigenic determinant, e.g. a unique determinant, from a protein represented by SEQ ID No:5.

A still further aspect of the present invention features an antibody preparation specifically reactive with an epitope of the cln57 immunogen.

In another aspect, the invention features an E6AP-binding protein referred to herein as "cln24". In preferred embodiments, the invention provides a substantially pure preparation of an cln24 polypeptide, or a recombinant cln24 polypeptide. As above, in preferred embodiments the cln24 polypeptide has a biological activity associated with its binding to E6AP, e.g., it retains the ability to bind to an E6AP protein, though it may be able to either agonize or antagonize assembly of E6AP-containing protein complexes. The polypeptide can be identical to the cln24 polypeptide shown in SEQ ID No:6, or it can merely be homologous to that sequence. For instance, the cln24 polypeptide preferably has an amino acid sequence at least 60% homologous to the amino acid sequence in SEQ ID No:6, though higher sequence homologies of, for example, 80%, 90% or 95% are also contemplated. The cln24 polypeptide can comprise the full length protein represented in SEQ ID No:6, or it can comprise a fragment of that protein, which fragment may be, for instance, at least 5, 10, 20, 50 or 100 amino acids in length. The cln24 polypeptide can be either an agonist (e.g. mimics), or alternatively, an antagonist of a biological activity of a naturally occurring form 50 or 100 amino acids in length. As described below, the cln25 polypeptide can be either an agonist (e.g. mimics), or alternatively, an antagonist of a biological activity of a naturally occurring form of the cln25 protein, e.g., the cln25 polypeptide is able to modulate E6AP-mediated regulation of cell cycle, differentiation and survival.

In a preferred embodiment, a peptide having at least one biological activity of the subject cln25 polypeptide may differ in amino acid sequence from the sequence in SEQ ID No:7, but such differences result in a modified protein which functions in the same or similar manner as the native E6AP-binding protein or which has the same or similar characteristics of the native E6AP-binding protein. However, homologs of the naturally occurring cln25 protein are contemplated which are antagonistic of the normal cellular role of the naturally occurring cln25 protein. For example, the homolog may be capable of interfering with the ability of E6AP to modulate degradation of cell cycle regulatory proteins, e.g., p53.

In yet other preferred embodiments, the E6AP-binding protein is a recombinant fusion protein which includes a second polypeptide portion, e.g., a second polypeptide having an amino acid sequence unrelated to cln25, e.g. the second polypeptide portion is glutathione-S-transferase, e.g. the second polypeptide portion is a DNA binding domain of transcriptional regulatory protein, e.g. the second polypeptide portion is an RNA polymerase activating domain, e.g. the fusion protein is functional in a two-hybrid assay.

Yet another aspect of the present invention concerns an immunogen comprising an cln25 peptide in an immunogenic preparation, the immunogen being capable of eliciting an immune response specific for said E6AP-BP polypeptide; e.g. a humoral response, e.g. an antibody response; e.g. a cellular response. In preferred embodiments, the immunogen comprising an antigenic determinant, e.g. a unique determinant, from a protein represented by SEQ ID No:7.

A still further aspect of the present invention features an antibody preparation specifically reactive with an epitope of the cln25 immunogen.

In still another aspect, the invention features an E6AP-binding protein referred to herein as "cln42". In preferred embodiments, the invention provides a substantially pure preparation of an cln42 polypeptide, or a recombinant cln42 polypeptide. In preferred embodiments the polypeptide has a biological activity associated with its binding to E6AP, e.g., it retains the ability to bind to an E6AP protein, though it may be able to either agonize or antagonize assembly of E6AP-containing protein complexes. The polypeptide can be identical to the cln42 polypeptide shown in SEQ ID No:8, or it can merely be homologous to that sequence. For instance, the cln42 polypeptide preferably has an amino acid sequence at least 60% homologous to the amino acid sequence in SEQ ID No:8, though higher sequence homologies of, for example, 80%, 90% or 95% are also contemplated. The cln42 of the cln24 protein, e.g., the cln24 polypeptide is able to modulate E6AP-mediated regulation of cell cycle, differentiation and survival.

In a preferred embodiment, a peptide having at least one biological activity of the subject cln24 polypeptide may differ in amino acid sequence from the sequence in SEQ ID No:6, but such differences result in a modified protein which functions in the same or similar manner as the native E6AP-binding protein or which has the same or similar characteristics of the native E6AP-binding protein. However, homologs of the naturally occurring cln24 protein are contemplated which are antagonistic of the normal cellular role of the naturally occurring cln24 protein. For example, the homolog may be capable of interfering with the ability of E6AP to modulate degradation of cell cycle regulatory proteins, e.g., p53.

In yet other preferred embodiments, the cln24 protein is a recombinant fusion protein which includes a second polypeptide portion, e.g., a second polypeptide having an amino acid sequence unrelated to cln24 protein, e.g. the second polypeptide portion is glutathione-S-transferase, e.g. the second polypeptide portion is a DNA binding domain of transcriptional regulatory protein, e.g. the second polypeptide portion is an RNA polymerase activating domain, e.g. the fusion protein is functional in a two-hybrid assay.

Yet another aspect of the present invention concerns an immunogen comprising a cln24 polypeptide in an immunogenic preparation, the immunogen being capable of eliciting an immune response specific for said polypeptide; e.g. a humoral response, e.g. an antibody response; e.g. a cellular response. In preferred embodiments, the immunogen comprising an antigenic determinant, e.g. a unique determinant, from a protein represented by SEQ ID No:6.

A still further aspect of the present invention features an antibody preparation specifically reactive with an epitope of the cln24 immunogen.

In another aspect, the invention features an E6AP-binding protein referred to herein as "cln25". In preferred embodiments, the invention provides a substantially pure preparation of an cln25 polypeptide, or a recombinant cln25 polypeptide. In preferred embodiments the polypeptide has a biological activity associated with its binding to E6AP, e.g., it remaits the ability to bind to an E6AP protein, though it may be able to either agonize or antagonize assembly of E6AP-containing protein complexes. The polypeptide can be identical to the cln25 polypeptide shown in SEQ ID No:7, or it can merely be homologous to that sequence. For instance, the cln25 polypeptide preferably has an amino acid sequence at least 60% homologous to the amino acid sequence in SEQ ID No:7, though higher sequence homologies of, for example, 80%, 90% or 95% are also contemplated. The cln25 polypeptide can comprise the full length protein represented in SEQ ID No:7, or it can comprise a fragment of that protein, which fragment may be, for instance, at least 5, 10, 20, polypeptide can comprise the full length protein represented in SEQ ID No:8, or it can comprise a fragment of that protein, which fragment may be, for instance, at least 5, 10, 20, 50 or 100 amino acids in length. As described below, the cln42 polypeptide can be either an agonist (e.g. mimics), or alternatively, an antagonist of a biological activity of a naturally occurring form of the cln42 protein, e.g., the cln42 polypeptide is able to modulate E6AP-mediated regulation of cell cycle, differentiation and survival.

In a preferred embodiment, a peptide having at least one biological activity of the subject cln42 polypeptide may differ in amino acid sequence from the sequence in SEQ ID No:8, but such differences result in a modified protein which functions in the same or similar manner as the native E6AP-binding protein or which has the same or similar characteristics of the native E6AP-binding protein. However, homologs of the naturally occurring cln42 protein are contemplated which are antagonistic of the normal cellular role of the naturally occurring cln42 protein. For example, the homolog may be capable of interfering with the ability of E6AP to modulate gene degradation of cell cycle regulatory proteins, e.g., p53.

In yet other preferred embodiments, the E6AP-binding protein is a recombinant fusion protein which includes a second polypeptide portion, e.g., a second polypeptide having an amino acid sequence unrelated to cln42, e.g. the second polypeptide portion is glutathione-S-transferase, e.g. the second polypeptide portion is a DNA binding domain of transcriptional regulatory protein, e.g. the second polypeptide portion is an RNA polymerase activating domain, e.g. the fusion protein is functional in a two-hybrid assay.

Yet another aspect of the present invention concerns an immunogen comprising an cln42 peptide in an immunogenic preparation, the immunogen being capable of eliciting an immune response specific for said E6AP-BP polypeptide; e.g. a humoral response, e.g. an antibody response; e.g. a cellular response. In preferred embodiments, the immunogen comprising an antigenic determinant, e.g. a unique determinant, from a protein represented by SEQ ID No:8.

A still further aspect of the present invention features an antibody preparation specifically reactive with an epitope of the cln42 immunogen.

Another aspect of the present invention provides a substantially isolated nucleic acid having a nucleotide sequence which encodes an cln57 polypeptide. In preferred embodiments: the encoded polypeptide specifically binds an E6AP protein and/or is able to either agonize or antagonize assembly of E6AP-containing protein complexes. The coding sequence of the nucleic acid can comprise a cln57-encoding sequence which can be identical to the cln57 cDNA shown in SEQ ID No:1, or it can merely be homologous to that sequence. For instance, the cln57-encoding sequence preferably has a sequence at least 60% homologous to the nucleotide sequence in SEQ ID No:1, though higher sequence homologies of, for example, 80%, 90% or 95% are also contemplated. The cln57 polypeptide encoded by the nucleic acid can comprise the nucleotide sequence represented in SEQ ID No:1 which encodes the full length protein, or it can comprise a fragment of that nucleic acid, which fragment may be, for instance, encode a fragment of cln57 which is, for example, at least 5, 10, 20, 50 or 100 amino acids in length. The cln57 polypeptide encoded by the nucleic acid can be either an agonist (e.g. mimics), or alternatively, an antagonist of a biological activity of a naturally occurring form of the cln57 protein, e.g., the cln57 polypeptide is able to modulate E6AP-mediated regulation of cell cycle, differentiation and survival.

Furthermore, in certain preferred embodiments, the subject cln57 nucleic acid will include a transcriptional regulatory sequence, e.g. at least one of a transcriptional promoter or transcriptional enhancer sequence, which regulatory sequence is operably linked to the cln57 gene sequence. Such regulatory sequences can be used in to render the cln57 gene sequence suitable for use as an expression vector.

In yet a further preferred embodiment, the nucleic acid hybridizes under stringent conditions to a nucleic acid probe corresponding to at least 12 consecutive nucleotides of SEQ ID No:1; preferably to at least 20 consecutive nucleotides of SEQ ID No:1; more preferably to at least 40 consecutive nucleotides of SEQ ID No:1.

Another aspect of the present invention provides a substantially isolated nucleic acid having a nucleotide sequence which encodes an cln24 polypeptide. In preferred embodiments: the encoded polypeptide specifically binds an E6AP protein and/or is able to either agonize or antagonize assembly of E6AP-containing protein complexes. The coding sequence of the nucleic acid can comprise a cln24-encoding sequence which can be identical to the cln24 cDNA shown in SEQ ID No:2, or it can merely be homologous to that sequence. For instance, the cln24-encoding sequence preferably has a sequence at least 60% homologous to the nucleotide sequence in SEQ ID No:2, though higher sequence homologies of, for example, 80%, 90% or 95% are also contemplated. The cln24 polypeptide encoded by the nucleic acid can comprise the nucleotide sequence represented in SEQ ID No:2 which encodes the full length protein, or it can comprise a fragment of that nucleic acid, which fragment may be, for instance, encode a fragment of cln24 which is, for example, at least 5, 10, 20, 50 or 100 amino acids in length. The cln24 polypeptide encoded by the nucleic acid can be either an agonist (e.g. mimics), or alternatively, an antagonist of a biological activity of a naturally occurring form of the cln24 protein, e.g., the cln24 polypeptide is able to modulate E6AP-mediated regulation of cell cycle, differentiation and survival.

Furthermore, in certain preferred embodiments, the subject cln24 nucleic acid will include a transcriptional regulatory sequence, e.g. at least one of a transcriptional promoter or transcriptional enhancer sequence, which regulatory sequence is operably linked to the cln24 gene sequence. Such regulatory sequences can be used in to render the cln24 gene sequence suitable for use as an expression vector.

In yet a further preferred embodiment, the nucleic acid hybridizes under stringent conditions to a nucleic acid probe corresponding to at least 12 consecutive nucleotides of SEQ ID No:2; preferably to at least 20 consecutive nucleotides of SEQ ID No:2; more preferably to at least 40 consecutive nucleotides of SEQ ID No:2.

Another aspect of the present invention provides a substantially isolated nucleic acid having a nucleotide sequence which encodes an cln25 polypeptide. In preferred embodiments: the encoded polypeptide specifically binds an E6AP protein and/or is able to either agonize or antagonize assembly of E6AP-containing protein complexes. The coding sequence of the nucleic acid can comprise a cln25-encoding sequence which can be identical to the cln25 cDNA shown in SEQ ID No:3, or it can merely be homologous to that sequence. For instance, the cln25-encoding sequence preferably has a sequence at least 60% homologous to the nucleotide sequence in SEQ ID No:3, though higher sequence homologies of, for example, 80%, 90% or 95% are also contemplated. The cln25 polypeptide encoded by the nucleic acid can comprise the nucleotide sequence represented in SEQ ID No:3 which encodes the full length protein, or it can comprise a fragment of that nucleic acid, which fragment may be, for instance, encode a fragment of cln25 which is, for example, at least 5, 10, 20, 50 or 100 amino acids in length. The cln25 polypeptide encoded by the nucleic acid can be either an agonist (e.g. mimics), or alternatively, an antagonist of a biological activity of a naturally occurring form of the cln25 protein, e.g., the cln25 polypeptide is able to modulate E6AP-mediated regulation of cell cycle, differentiation and survival.

Furthermore, in certain preferred embodiments, the subject cln25 nucleic acid will include a transcriptional regulatory sequence, e.g. at least one of a transcriptional promoter or transcriptional enhancer sequence, which regulatory sequence is operably linked to the cln25 gene sequence. Such regulatory sequences can be used in to render the cln25 gene sequence suitable for use as an expression vector.

In yet a further preferred embodiment, the nucleic acid hybridizes under stringent conditions to a nucleic acid probe corresponding to at least 12 consecutive nucleotides of SEQ ID No:3; preferably to at least 20 consecutive nucleotides of SEQ ID No:3; more preferably to at least 40 consecutive nucleotides of SEQ ID No:3.

Another aspect of the present invention provides a substantially isolated nucleic acid having a nucleotide sequence which encodes an cln42 polypeptide. In preferred embodiments: the encoded polypeptide specifically binds an E6AP protein and/or is able to either agonize or antagonize assembly of E6AP-containing protein complexes. The coding sequence of the nucleic acid can comprise a cln42-encoding sequence which can be identical to the cln42 cDNA shown in SEQ ID No:4, or it can merely be homologous to that sequence. For instance, the cln42-encoding sequence preferably has a sequence at least 60% homologous to the nucleotide sequence in SEQ ID No:4, though higher sequence homologies of, for example, 80%, 90% or 95% are also contemplated. The cln42 polypeptide encoded by the nucleic acid can comprise the nucleotide sequence represented in SEQ ID No:4 which encodes the full length protein, or it can comprise a fragment of that nucleic acid, which fragment may be, for instance, encode a fragment of cln42 which is, for example, at least 5, 10, 20, 50 or 100 amino acids in length. The cln42 polypeptide encoded by the nucleic acid can be either an agonist (e.g. mimics), or alternatively, an antagonist of a biological activity of a naturally occurring form of the cln42 protein, e.g., the cln42 polypeptide is able to modulate E6AP-mediated regulation of cell cycle, differentiation and survival.

Furthermore, in certain preferred embodiments, the subject cln42 nucleic acid will include a transcriptional regulatory sequence, e.g. at least one of a transcriptional promoter or transcriptional enhancer sequence, which regulatory sequence is operably linked to the cln42 gene sequence. Such regulatory sequences can be used in to render the cln42 gene sequence suitable for use as an expression vector.

In yet a further preferred embodiment, the nucleic acid hybridizes under stringent conditions to a nucleic acid probe corresponding to at least 12 consecutive nucleotides of SEQ ID No:4; preferably to at least 20 consecutive nucleotides of SEQ ID No:4; more preferably to at least 40 consecutive nucleotides of SEQ ID No:4.

The invention also features transgenic non-human animals, e.g. mice, rats, rabbits or pigs, having a transgene, e.g., animals which include (and preferably express) a heterologous form of one of the E6AP-BP genes described herein, e.g. a gene derived from humans, or which misexpress an endogenous E6AP-BP gene, e.g., an animal in which expression of one or more of the subject E6AP-binding proteins is disrupted. Such a transgenic animal can serve as an animal model for studying cellular disorders comprising mutated or mis-expressed E6AP-BP alleles or for use in drug screening.

The invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of one of SEQ ID Nos:1-4, or naturally occurring mutants thereof. In preferred embodiments, the probe/primer further includes a label group attached thereto and able to be detected. The label group can be selected, e.g., from a group consisting of radio-isotopes, fluorescent compounds, enzymes, and enzyme co-factors. Probes of the invention can be used as a part of a diagnostic test kit for identifying transformed cells, such as for detecting in a sample of cells isolated from a patient, a level of a nucleic acid encoding one of the subject E6AP-binding proteins; e.g. measuring the E6AP-BP mRNA level in a cell, or determining whether the genomic E6AP-BP gene has been mutated or deleted. Preferably, the oligonucleotide is at least 10 nucleotides in length, though primers of 20, 30, 50, 100, or 150 nucleotides in length are also contemplated.

In yet another aspect, the invention provides an assay for screening test compounds for an inhibitors, or alternatively, potentiators, of an interaction between an E6AP-binding protein and an E6AP protein. An exemplary method includes the steps of (i) combining a cellular E6AP protein, an E6AP-BP, e.g., an E6AP-BP of the invention (e.g. a protein expressed from one of the clones selected from the group cln57, cln24, cln25, and cln42), and a test compound, e.g., under conditions wherein, but for the test compound, the E6AP protein and the E6AP-binding protein are able to interact; and (ii) detecting the formation of a complex which includes the E6AP protein and the E6AP-binding protein. A statistically significant change, such as a decrease, in the formation of the complex in the presence of a test compound (relative to what is seen in the absence of the test compound) is indicative of a modulation, e.g., inhibition, of the interaction between E6AP and the E6AP-binding protein. Moreover, primary screens are provided in which the E6AP protein and the E6AP-binding protein are combined in a cell-free system and contacted with the test compound; i.e. the cell-free system is selected from a group consisting of a cell lysate and a reconstituted protein mixture. Alternatively, E6AP and the E6AP-binding protein are simultaneously expressed in a cell, and the cell is contacted with the test compound, e.g. as an interaction trap assay (two hybrid assay).

The present invention also provides a method for treating an animal having unwanted cell growth characterized by a mis-expression of one or more of the subject E6AP-binding proteins. For instance, in one embodiment, the method comprises administering a therapeutically effective amount of an agent able to inhibit the interaction of the E6AP-binding protein with other cellular or viral proteins. Alternatively, antagonistic forms of the subject proteins can be expressed in the cell, or expression of an E6AP-BP gene disrupted by antisense therapy.

For instance, the invention features E6AP-BP antisense constructs which, by inhibiting expression of one of the E6AP-BP gene products, can modulate cellular p53 levels in $p53^+$ epithelial cells. By manipulation (e.g., activation) of this cell-cycle checkpoint, proliferation or other mitotic and/or transcriptional activity of a cell can be modulated by the subject antisense constructs. Accordingly, the compositions of the present invention can be used to regulate cell proliferation and/or viability in both cell cultures and in animals. The E6AP-BP antisense constructs can be used to modulate proliferation of ectodermally-derived tissue/cells, such as epithelial cells. For instance, the present invention provides methods for treating papillomavirus (PV) infected cells, including PV-transformed cells. Furthermore, the subject compositions can be used to regulate proliferation of epithelial tissues, both transformed and non-transformed, such as in wound repair processes, proliferative skin disorders, and protection against cytotoxic agents.

Another aspect of the present invention provides a method of determining if a subject, e.g. a human patient, is at risk for a disorder characterized by unwanted cell proliferation. The method includes detecting, in a tissue of the subject, the presence or absence of a genetic lesion characterized by at least one of (i) a mutation of a gene encoding a protein represented by one of SEQ ID Nos: 5-8, or a homolog thereof; (ii) the mis-expression of a gene encoding a protein represented by one of SEQ ID Nos: 5-8; or (iii) the mis-incorporation of an E6AP-binding protein in a transcriptional regulatory complex comprising an E6AP protein. In preferred embodiments: detecting the genetic lesion includes ascertaining the existence of at least one of: a deletion of one or more nucleotides from the E6AP-BP gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; or a non-wild type level of the protein.

For example, detecting the genetic lesion can include (i) providing a probe/primer including an oligonucleotide containing a region of nucleotide sequence which hybridizes to a sense or antisense sequence of one of SEQ ID Nos: 1-4, or naturally occurring mutants thereof or 5' or 3' flanking sequences naturally associated with the E6AP-BP gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the E6AP-BP gene and, optionally, of the flanking nucleic acid sequences. For instance, the probe/primer can be employed in a polymerase chain reaction (PCR) or in a ligation chain reaction (LCR). In alternate embodiments, the level of the E6AP-binding protein is detected in an immunoassay using an antibody which is specifically immunoreactive with a protein represented by one of SEQ ID Nos: 5-8.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following detailed description, and from the claims.

DESCRIPTION OF THE DRAWINGS

FIG. 2A is sequence alignment of a portion of the cln57 protein (SEQ ID NO: 5) and the HPV E6 protein (SEQ ID NO: 15).

DETAILED DESCRIPTION OF THE INVENTION

Figure 1:
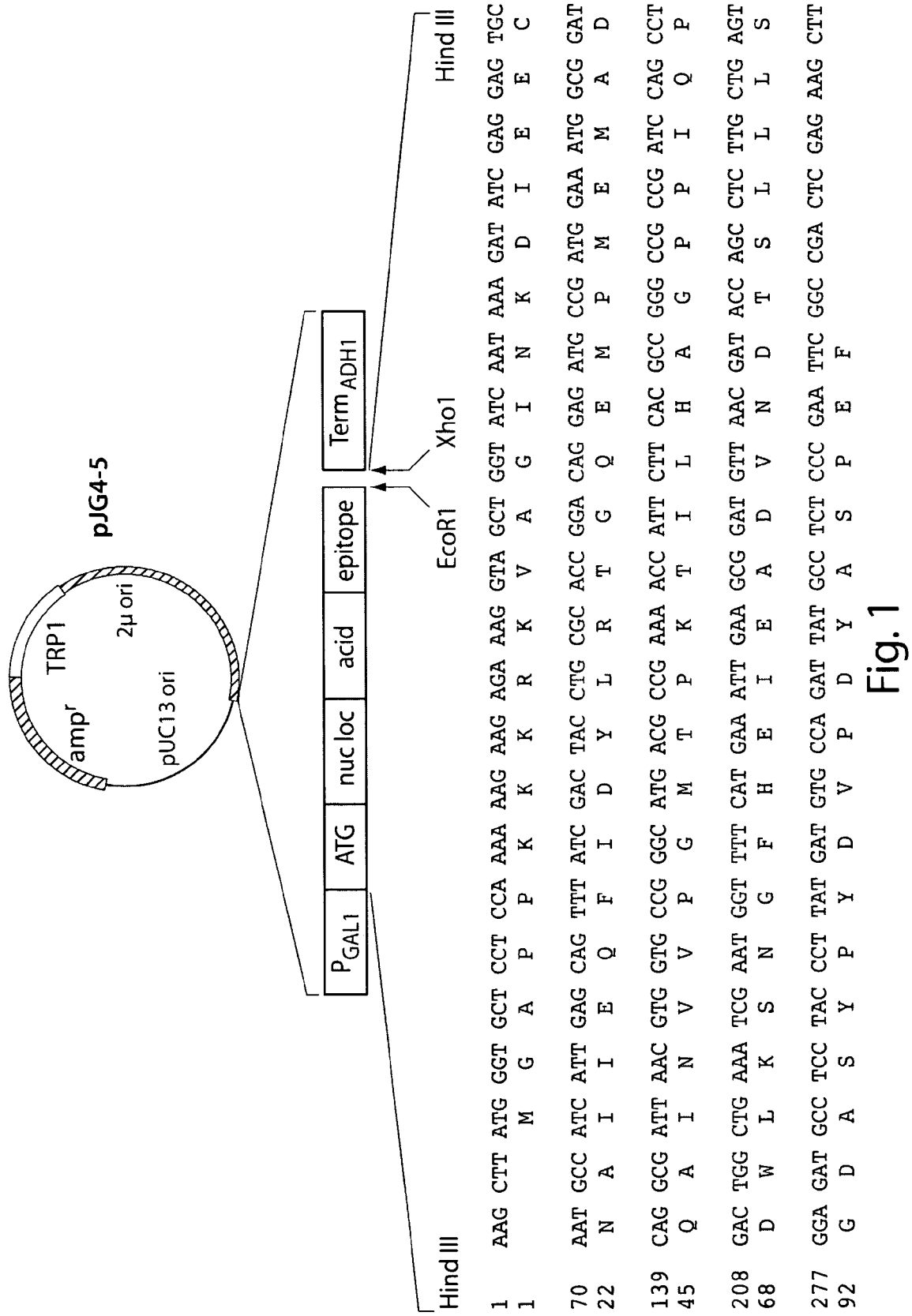
FIG. 1 illustrates the pJG4-5 library plasmid and the invariant 107 amino acid moiety (SEQ ID NO. 14) it encodes. This moiety carries (amino to carboxy termini) an ATG, an SV40 nuclear localization sequence (PPKKKRKVA) (SEQ ID No:9), the B42 transcription activation domain, and the HA1 epitope tag (YPYDVPDYA) (SEQ ID No:10). pJG4-5 directs the synthesis of proteins under the control of the GAL1 promoter. It carries a 2µ replicator and a TRP1$^+$ selectable marker. Each of the E6AP-binding proteins are inserted as EcoRI-XhoI fragments. Downstream of the XhoI site, pJG4-5 contains the ADH1 transcription terminator.

The ubiquitin system is essential for a wide spectrum of cellular phenomena, and is a component of many biological regulatory mechanisms, including aspects of growth control, metabolic regulation, embryonic development, and cell-cycle progression.

The present invention relates to the discovery in eukaryotic cells, particularly human cells, of novel protein-protein interactions between certain cellular proteins, referred to herein as "E6AP-binding proteins" or "E6AP-BPs", and the cellular protein E6AP, the latter of which is a component of a ubiquitin-ligase (E3) enzyme. The association of E6AP and the subject E6AP-binding proteins implicates the E6AP-binding proteins in a number of basic cellular functions, such as regulation of gene expression, regulation of the cell-cycle, modification of cell surface receptors, biogenesis of ribosomes, and DNA repair. One apparent function for certain members of this family of proteins involves a role in ubiquitin-mediated systems, as for example in the control of cellular half-lives of various proteins. For instance, certain of the E6AP-binding proteins, such as the protein identified herein as cln57, are implicated in the ubiquitin-mediated inactivation of cell-cycle regulatory proteins, e.g., p53, p27 and/or cyclins, as proteins which facilitate or otherwise regulate the transfer of ubiquitin. The roles of these proteins can include participation in ubiquitination as, for example, allosteric or catalytic subunits of ubiquitin ligating complexes, or as associate proteins which direct specificity. In addition, the subject proteins may themselves be regulatory proteins which are substrates of ubiquitination by E6AP complexes. Consequently, the present invention identifies potential molecular targets, e.g., the interaction between E6AP and E6AP-binding proteins, for regulating the E6AP-mediated processes and thereby modulating, for instance, cell proliferation, cell differentiation, apoptosis and/or cellular sensitivity to chemotherapeutics and DNA damaging agents.

One important feature of the gene and gene product reported herein as "cln57" is the 50+ stretch of amino acid residues in the cln57 sequence which share 40% identity and 59% similarity to the papillomavirus E6 protein (see FIGS.

2A and 2B). As set out below, the implication of this homology, along with the ability of the cln57 protein to bind to E6-AP is strongly suggestive that this protein is the human cellular ortholog of the viral E6 protein.

Accordingly, the present invention makes available diagnostic and therapeutic assays, reagents and kits for detecting and treating proliferative and/or diifferentiative disorders arising from, for example, tumorogenic transformation of cells, or other hyperplastic or neoplastic transformation processes. For example, the present invention makes available reagents, such as antibodies and nucleic acid probes, for detecting altered complex formation, and/or altered levels of expression of the subject E6AP-binding proteins, and/or E6AP-BP gene deletion or mutation, in order to identify cells undergoing aberrant proliferation, e.g. transformed cells. Moreover, the present invention provides a method of treating a wide variety of pathological cell proliferative conditions, such as by gene therapy utilizing recombinant gene constructs encoding the subject E6AP-BP polypeptides (either agonistic or antagonistic forms), by providing peptidomimetics which either inhibit or potentiate the interaction between E6AP-BP and E6AP, or by providing inhibitors of the catalytic activity of any of the subject E6AP-binding proteins which are enzymes. In addition to therapeutic uses, such methods and reagents can also be used in tissue culture, such as to regulate the transformation of cells in vitro.

As described herein, an E6AP-dependent interaction trap assay was used to identify cellular proteins that can associate with the human E6AP protein. A number of novel proteins which interact with E6AP were cloned from a human cDNA library. Given the apparent role of E6AP in mediating ubiquitin conjugation to cellular and viral proteins, the present data suggests that E6AP is an important core protein of various multimeric complexes, with multiple cellular proteins participating in E6AP assembled complexes to control the activation and inactivation of, for example, growth and developmental regulatory proteins. This invention, as described below, therefore derives in part from the discovery that, in addition to the tumor suppressor protein p53, and the papillomavirus E6 protein, the cellular protein E6AP is also associated with several other cellular proteins (hereinafter termed "cellular E6AP-binding proteins" or "E6AP-BPs"), which association is likely to be involved in normal cell homeostasis, as well as the pathogenesis of various proliferative and differentiative disorders. Consequently, the interaction of E6AP with one or more of the subject E6AP-binding proteins may be significant in the regulation of cell-cycle progression, differentiation and survival. Other aspects of the invention are described below or will be apparent to those skilled in the art in light of the present disclosure.

For convenience, certain terms employed in the specification, examples, and appended claims are collected here.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

As used herein, the term "gene" or "recombinant gene" refers to a nucleic acid comprising an open reading frame encoding an E6AP-binding protein of the present invention, including both exon and (optionally) intron sequences. A "recombinant gene" refers to nucleic acid encoding an E6AP-binding protein and comprising E6AP-BP encoding exon sequences, though it may optionally include intron sequences which are either derived from a chromosomal E6AP-BP gene or from an unrelated chromosomal gene. Exemplary recombinant genes encoding the subject E6AP-binding proteins are represented by any one of SEQ ID Nos: 1-4. The term "intron" refers to a DNA sequence present in a given E6AP-BP gene which is not translated into protein and is generally found between exons.

As used herein, the term "transfection" means the introduction of a nucleic acid, e.g., an expression vector, into a recipient cell by nucleic acid-mediated gene transfer.

As used herein, "proliferating" and "proliferation" refer to cells undergoing mitosis.

As used herein, "transformed cells" is art recognized and refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control. In general, term "transformed cell" refers to cells which exhibit at least the following properties: (i) increased capacity to persist in serial subcultures; (ii) increased growth rate in vitro, and (iii) loss of contact inhibition.

The term "immortal cell" or "immortalized cell" is art recognized, and is used to refer to transformed cells which are able to persist in serial subcultures indefinitely.

The term "normal cell" is art recognized and refers to cells that are not transformed. Preferably, normal cells do not have increased capacity to persist in serial subcultures or increased growth rate in vitro. Normal cells when grown in cultures do not exhibit loss of contact inhibition.

The term "p53+" refers to a cell in which express of p53, or mutants thereof, occurs, though it will be understood that the half-life of the protein can vary greatly. This is in contrast to "p53−" cells in which expression of the p53 gene has been disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant E6AP-BP gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the E6AP-binding protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of an epithelial lineage, e.g., cervical squamous cells. The term also covers so-called "leaky" promoters, which regulate expression of a selected DNA primarily in one tissue, but cause expression in other tissues as well.

As used herein, a "transgenic animal" is any animal, preferably a non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of a subject E6AP-binding protein, e.g. either agonistic or antagonistic forms. However, transgenic animals in which the recombinant E6AP-BP gene is silent are also contemplated, as for example, the FLP or CRE recombinase dependent constructs described below. The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the *Xenopus* genus, and transgenic chickens can also provide important tools for understanding, for example, embryogenesis and tissue patterning. The term "chimeric animal" is used herein to refer to animals in which the recombinant gene is found, or in which the recombinant is expressed in some but not all cells of the animal. The term "tissue-specific chimeric animal" indicates that the recombinant E6AP-BP gene is present and/or expressed in some tissues but not others.

As used herein, the term "transgene" means a nucleic acid sequence (encoding, e.g., an E6AP-binding protein), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As used herein, the term "specifically hybridizes" refers to the ability of antisense constructs, including probes and primers, of the present invention to bind under cellular conditions, e.g., physiological conditions present in a given cell, with the cellular mRNA and/or genomic DNA encoding a E6AP-BP gene so as to inhibit expression of that protein, e.g. by inhibiting transcription and/or translation. Such hybridization should be selective to a specific E6AP-BP gene, e.g., resulting in hybridization to other genes, under cellular conditions at a level of less than 25% relative to hybridization to the E6AP-BP gene, more preferably less than 10% and even more preferably less than 5%. For instance, antisense constructs of the present invention are preferably at least 50% homologous to the nucleotide sequence of an E6AP-BP gene, more preferably at least 70% homologous to the nucleotide sequence of an E6AP-BP gene and most preferably at least 90% homologous to the nucleotide sequence of an E6AP-BP gene. Of course, antisense constructs identical to the complementary strand of SEQ ID No. 1, 2, 3 or 4 are more preferred.

As used herein the term "suppressing tumor growth" refers to the ability of an E6AP-BP polypeptide, or nucleic acid construct of the present invention to, by modulating cellular levels of a regulatory protein, inhibit proliferation of transformed cells. For example, upregulation of p53 levels in certain p53+ tumor cells, e.g., HPV-infected or HPV-transformed can cause apoptosis of the cells.

As used herein the term "antisense construct" refers to both the ex vivo generated oligonucleotide and the gene therapy constructs described herein.

The term "ectoderm" refers to the outermost of the three primitive germ layers of the embryo; from it are derived the epidermis and epidermal tissues such as the nails, hair and glands of the skin, the nervous system, external sense organs and mucous membrane of the mouth and anus.

The terms "epithelia" and "epithelium" refer to the cellular covering of internal and external body surfaces (cutaneous, mucous and serous), including the glands and other structures derived therefrom, e.g., corneal, esophegeal, epidermal, and hair follicle epithelial cells. Other exemplary epithelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, which that characteristically found lining hollow organs that are subject to great mechanical change due to contraction and distention, e.g. tissue which represents a transition between stratified squamous and columnar epithelium. The term "epithelialization" refers to healing by the growth of epithelial tissue over a denuded surface.

Furthermore, the term "epithelioid cells" refers to cells which have phenotypes resembling epithelial cells. For instance, epithelioid cells can be cells from an epithelioma or other epitheliomatous cells, e.g. any tumor derived from epithelium, such as a carcinoma.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Another carcinomatous epithelial growth is "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "epidermis" refers to the outermost and nonvascular layer of the skin, derived from the embryonic ectoderm, varying in thickness from 0.07-1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent. An "epidermoid" is a cell or tissue resembling the epidermis, but may also be used to refer to any tumor occurring in a noncutaneous site and formed by inclusion of epidermal elements.

The term "hair" (or "pilus") refers to a threadlike structure, especially the specialized epidermal structure composed of keratin and developing from a papilla sunk in the corium, produced only by mammals and characteristic of that group of animals. Also, the aggregate of such hairs. A "hair follicle" refers to one of the tubular-invaginations of the epidermis enclosing the hairs, and from which the hairs grow; and "hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis, such as "epidermodysplasia verruciformis", which is a condition due to a virus identical with or closely related to the virus of common warts. Another example is "epidermolysis", which refers to a loosened state of the epidermis with formation of blebs and bullae either spontaneously or at the site of trauma.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

The term "cosmetic preparation" refers to a form of a pharmaceutical preparation which is formulated for topical administration.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding an E6AP-binding protein" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject E6AP-binding proteins with a second amino acid sequence defining a domain foreign to and not substantially homologous with the E6AP-BP from which the first amino acid sequence is derived. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-Y-Z, wherein Y represents a portion of the fusion protein which is derived from an one of the subject E6AP-binding protein, and X and Z each represent polypeptide sequences which are heterologous to the E6AP-BP sequence, at least one of X and Z being present in the fusion protein.

The term "evolutionarily related to", with respect to nucleic acid sequences encoding E6AP-binding protein, refers to nucleic acid sequences which have arisen naturally in an organism, including naturally occurring mutants. The term also refers to nucleic acid sequences which, while derived from a naturally occurring E6AP-BP, have been altered by mutagenesis, as for example, combinatorial mutagenesis described below, yet still encode polypeptides which have at least one activity of an E6AP-binding protein.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding one of the subject E6AP-binding proteins preferably includes no more than 10 kilobases (kb) of nucleic acid sequence which naturally immediately flanks that particular E6AP-BP gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As described below, one aspect of the invention pertains to an isolated nucleic acid having a nucleotide sequence encoding one of the subject E6AP-binding proteins, and/or equivalents of such nucleic acids. The term equivalent is understood to include nucleotide sequences encoding functionally equivalent E6AP-binding proteins or functionally equivalent polypeptides which, for example, retain the ability to bind to E6AP. Equivalent nucleotide sequences will include sequences that differ by one or more nucleotide substitutions, additions or deletions, such as allelic variants; and will, therefore, include sequences that differ from the nucleotide sequence of the E6AP-BP genes shown in any of SEQ ID Nos: 1-4 due to the degeneracy of the genetic code. Equivalents will also include nucleotide sequences that hybridize under stringent conditions (i.e., equivalent to about 20-27° C. below the melting temperature ($T_m$) of the DNA duplex formed in about IM salt) to the nucleotide sequence of an E6AP-BP gene represented in one of SEQ ID Nos: 1-4. In one embodiment, equivalents will further include nucleic acid sequences derived from and evolutionarily related to, a nucleotide sequences shown in any of SEQ ID Nos: 1-4.

Polypeptides referred to herein as having an activity of an E6AP-binding protein are polypeptides that have an amino acid sequence identical or homologous to all or a portion of a polypeptide designated by one of SEQ ID No:5-8, and may be generally characterized as capable of binding to E6AP. The above notwithstanding, such polypeptides may also be distinguished by: an ability to mediate ubiquitination of cellular proteins, e.g. cell-cycle regulatory proteins; an ability to mediate ubiquitin-dependent degradation of cellular proteins, e.g. cell-cycle regulatory proteins; an ability to affect the cellular half-life of a cell-cycle regulatory protein, such as p53, p27 or a cyclin, e.g. in normal cells, e.g. in normal proliferating cells, e.g. in virally-infected cells, e.g. in papillomavirus infected cells, e.g. in HPV-infected cells, e.g. in HPV-16, HPV-18, HPV-31, or HPV-33 infected cells, e.g. in cells expressing a papillomavirus E6 protein, e.g. in transformed cells, e.g. in cancerous cells. Other biological activities of the subject E6AP-binding proteins are described herein or will be reasonably apparent to those skilled in the art.

Moreover, it will be generally appreciated that, under certain circumstances, it may be advantageous to provide homologs of the subject E6AP-binding proteins which function in a limited capacity as one of either an agonists (e.g., mimetic) or an antagonist of the normal bioactivity of the wild-type protein, in order to promote or inhibit only a subset of the biological activities of the wild-type form of the protein. Thus, specific biological effects can be elicited by treatment with a homolog of limited function, and with fewer side effects relative to treatment with homologs retaining or inhibiting all of the biological activity of a E6AP-binding protein. For instance, antagonistic homologs can be generated which interfere with the ability of certain of the wild-type ("authentic") E6AP-binding proteins to form complexes with E6AP, but which do not substantially interfere with the formation of complexes between the E6AP-BP and other cellular proteins, such as may be involved in other regulatory mechanisms of the cell.

Homologs of the subject E6AP-binding proteins can be generated by mutagenesis, such as by discrete point mutation(s), or by truncation. For instance, mutation can give rise to homologs which retain substantially the same, or merely a subset, of the biological activity of the E6AP-BP from which it was derived. Alternatively, antagonistic forms of the protein can be generated which are able to inhibit the function of the naturally occurring form of the protein, such as by competitively binding to E6AP.

Preferred nucleic acids encode an E6AP-binding protein comprising an amino acid sequence at least 60% homologous, more preferably at least 70% homologous and most preferably at least 80% homologous with an amino acid sequence designated by one of SEQ ID Nos: 5-8. Nucleic acids which encode polypeptides having an activity of a subject E6AP-binding protein and having at least about 90%, more preferably at least about 95%, and most preferably at least about 98-99% homology with a sequence shown in one of SEQ ID Nos: 5-8 are also within the scope of the invention, as of course are proteins which are identical to the aforementioned sequence listings. In one embodiment, the nucleic acid is a cDNA encoding a polypeptide having at least one activity of a subject E6AP-binding protein. Preferably, the nucleic acid is a cDNA molecule comprising at least a portion of the nucleotide sequence represented in one of SEQ ID Nos: 1-4. A preferred portion of these cDNA molecules includes the coding region of the gene.

Another aspect of the invention provides a nucleic acid which hybridizes under high or low stringency conditions to a DNA or RNA which encodes a polypeptide having all or a portion of an amino acid sequence shown in one of SEQ ID No:5, SEQ ID No:6, SEQ ID No:7, or SEQ ID No:8. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Nucleic acids having sequences which differ from the nucleotide sequences shown in any of SEQ ID Nos: 1-4 due to degeneracy in the genetic code are also within the scope of the invention. Such nucleic acids encode functionally equivalent polypeptides (i.e., polypeptides having a biological activity of an E6AP-binding protein) but that differ in sequence from the enumerated sequence listings due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of the E6AP-binding protein. However, it is expected that DNA sequence polymorphisms that do lead to changes in the amino acid sequences of the subject E6AP-binding proteins will exist among vertebrates. One skilled in the art will appreciate that these variations in one or more nucleotides (up to about 3-5% of the nucleotides) of the nucleic acids encoding polypeptides having an activity of an E6AP-binding protein may exist among individuals of a given species due to natural allelic variation. Any and all such nucleotide variations and resulting amino acid polymorphisms are within the scope of this invention.

Also contemplated are fragments of the coding sequences which provide active portions of the subject E6AP-binding proteins. As used herein, a fragment of a nucleic acid encoding an active portion of an E6AP-binding protein refers to an oligonucleotide having fewer nucleotides than the full length coding sequence for an E6AP-binding protein, but which nevertheless encodes a polypeptide possessing an E6AP-BP biological activity, e.g. the fragment retains the ability to bind to an E6AP protein. Nucleic acid fragments within the scope of the present invention include those capable of hybridizing under high or low stringency conditions with nucleic acids from other species such as may be used in screening protocols to detect E6AP-BP homologs, as well as probes capable of hybridizing with nucleic acids from human specimens for use in detecting the presence of a nucleic acid encoding one of the subject E6AP-BPs, including alternate isoforms, e.g. mRNA splicing variants. Nucleic acids within the scope of the invention may also contain linker sequences, modified restriction endonuclease sites and other sequences useful for molecular cloning, expression or purification of recombinant forms of the subject E6AP-binding proteins.

As indicated by the examples set out below, a nucleic acid encoding an E6AP-binding protein, or a homologous gene thereof, may be obtained from mRNA present in any of a number of eukaryotic cells. It should also be possible to obtain nucleic acids encoding E6AP-binding proteins of the present invention from genomic DNA obtained from both adults and embryos. For example, a gene encoding an E6AP-binding protein can be cloned from either a cDNA or a genomic library in accordance with protocols herein described, as well as those generally known to persons skilled in the art. A cDNA encoding an E6AP-binding protein can be obtained by isolating total mRNA from a cell, e.g. a mammalian cell, e.g. a human cell, including tumor cells. Double stranded cDNAs can then be prepared from the total mRNA, and subsequently inserted into a suitable plasmid or bacteriophage vector using any one of a number of known techniques. The gene encoding the E6AP-binding protein can also be cloned using established polymerase chain reaction techniques in accordance with the nucleotide sequence information provided by the invention. The nucleic acid of the invention can be DNA or RNA. A preferred nucleic acid is a cln57 cDNA represented by the sequence shown in SEQ ID No: 1. Another nucleic acid is a cln24 cDNA represented by the sequence shown in SEQ ID No: 2. Other preferred nucleic acids include cDNA molecules represented by the sequences shown in one of SEQ ID Nos: 3-4.

Another aspect of the invention relates to the use of the isolated nucleic acids for "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding an E6AP-binding protein so as to inhibit expression of that protein, as for example by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes an E6AP-binding protein. Alternatively, the antisense construct can be an oligonucleotide probe which is generated ex vivo and which, when introduced into the cell causes inhibition of expression by hybridizing with the mRNA and/or genomic sequences of an E6AP-BP gene. Such oligonucleotide probes are preferably modified oligonucleotides which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al. (1988) *Biotechniques* 6:958-976; and Stein et al. (1988) *Cancer Res* 48:2659-2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

Likewise, the antisense constructs of the present invention, by antagonizing the normal biological activity of an E6AP-binding protein, can be used in the manipulation of tissue, e.g. tissue differentiation, both in vivo and in ex vivo tissue cultures.

This invention also provides expression vectors containing a nucleic acid encoding a polypeptide having an activity of an E6AP-binding protein, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of a recombinant E6AP-binding protein. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences-sequences that control the expression of a DNA sequence when operatively linked to it may be used in these vectors to express DNA sequences encoding the E6AP-binding proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered. In one embodiment, the expression vector includes a recombinant gene encoding a polypeptide which mimics or otherwise agonizes the action of an E6AP-binding protein, or alternatively, which encodes a polypeptide that antagonizes the action of an authentic E6AP-binding protein. Such expression vectors can be used to transfect cells and thereby produce polypeptides, including fusion proteins, encoded by nucleic acids as described herein.

Moreover, the gene constructs of the present invention can also be used as a part of a gene therapy protocol to deliver nucleic acids encoding either an agonistic or antagonistic form of one or more of the subject E6AP-binding proteins. Thus, another aspect of the invention features expression vectors for in vivo transfection and expression of an E6AP-binding protein in particular cell types so as to reconstitute the function of, or alternatively, abrogate the function of one or more of the subject E6AP-binding proteins in a cell in which that protein or other transcriptional regulatory proteins to which it bind are misexpressed. For example, gene therapy can be used to deliver a gene encoding an E6AP-binding protein which inhibits degradation of cell cycle regulatory proteins such as p53.

Expression constructs of the subject E6AP-binding proteins, and mutants thereof, as well as antisense contructs, may be administered in any biologically effective carrier, e.g. any formulation or composition capable of effectively delivering the E6AP-BP gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of E6AP-BP expression are also useful for in vitro transduction of cells, such as for use in a diagnostic assays.

A preferred approach for in vivo introduction of nucleic acid into a cell is by use of a viral vector containing nucleic acid, e.g. a cDNA, encoding the E6AP-binding protein or homolog thereof. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up the vector.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding one of the subject receptors rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψcrip, ψCre, ψ2 and ψAm. Retroviruses have been used to introduce a variety of genes into many different cell types, including epithelial cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. No. 4,868,116; U.S. Pat. No. 4,980,286; PCT/US89/1422; PCT/US88/3089; PCT/US88/4383; and PCT/US91/8127.

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079-9083; Julan et al. (1992) *J. Gen Virol* 73:3251-3255; and Goud et al. (1983) *Virology* 163: 251-254); or coupling cell surface receptor ligands to the viral env proteins (Neda et al. (1991) *J. Biol Chem* 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the E6AP-BP gene of the retroviral vector.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109-127). Expression of the inserted E6AP-BP gene can be under control of, for example, the E1A promoter, the major late promoter (MLP) and associated leader sequences, the E3 promoter, or exogenously added promoter sequences.

Yet another viral vector system useful for delivery of the subject E6AP-BP genes is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

Other viral vector systems that may have application in gene therapy have been derived from herpes virus, vaccinia virus, and several RNA viruses. In particular, herpes virus vectors may provide a unique strategy for persistance of the recombinant E6AP-BP genes in cells of the central nervous system and occular tissue (Pepose et al. (1994) *Invest Ophthalmol Vis Sci* 35:2662-2666).

In addition to viral transfer methods, such as those illustrated above, non-viral methods can also be employed to cause expression of an E6AP-binding protein, or an antisense message, in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject E6AP-BP gene by the targeted cell. Exemplary gene delivery systems of this type include liposomal derived systems, poly-lysine conjugates, and artificial viral envelopes.

In a representative embodiment, a therapeutic E6AP-BP gene can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547-551; PCT publication WO91/06309; Japanese patent application 1047381; and European patent publication EP-A-43075). For example, lipofection of papilloma-virus infected epithelial cells can be carried out using liposomes tagged with monoclonal antibodies against, for example, the squamous cells.

In clinical settings, the gene delivery systems for the therapeutic E6AP-BP gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal, being quite localized to a particular tissue or organ. For example, the gene delivery vehicle can be introduced by catheter (see U.S. Pat. No. 5,328,470) or by stereotactic injection (e.g. Chen et al. (1994) *PNAS* 91: 3054-3057). To illustrate, an antagonistic form of one of the subject E6AP-binding proteins, such as the fragment of the cln57 clone described in the examples below, or an antisense construct specific for one of the subject E6-BP genes, can be delivered in a gene therapy construct to a cell by electroporation using techniques described, for example, by Dev et al. ((1994) *Cancer Treat Rev* 20:105-115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system. In the case of the latter, methods of introducing the viral packaging cells may be provided by, for example, rechargable or biodegradable devices. The generation of such implants is generally known in the art. See, for example, *Concise Encyclopedia of Medical & Dental Materials*, ed. by David Williams (MIT Press: Cambridge, Mass., 1990); Sabel et al. U.S. Pat. No. 4,883,666; Aebischer et al. U.S. Pat. No. 4,892,538; Aebischer et al. U.S. Pat. No. 5,106,627; Lim U.S. Pat. No. 4,391,909; Sefton U.S. Pat. No. 4,353,888; and Aebischer et al. (1991) *Biomaterials* 12:50-55).

Another aspect of the present invention concerns recombinant forms of the subject E6AP-binding proteins which are encoded by genes derived from higher eukaryotic organisms, e.g. mammals, e.g. humans, and which possess at least one biological activity of a naturally occurring form of the protein, or is an antagonist thereof (including naturally occurring dysfunctional mutants). The term "recombinant protein" refers to a protein of the present invention which is produced by recombinant DNA techniques, wherein generally DNA encoding the subject E6AP-binding protein is inserted into a suitable expression vector which is in turn used to transform a host cell to produce the heterologous protein. Moreover, the phrase "derived from", with respect to a recombinant gene, is meant to include within the meaning of "recombinant protein" those proteins having an amino acid sequence of a native E6AP-binding protein, or an amino acid sequence similar thereto which is generated by mutations including substitutions and deletions (including truncation). Recombinant proteins preferred by the present invention, in addition to native E6AP-binding proteins, are at least 60% homologous, more preferably 70% homologous and most preferably 80% homologous with an amino acid sequence shown in one of SEQ ID Nos:5-8. Polypeptides having an activity of the subject E6AP-binding proteins (i.e. either agonistic or antagonistic of the naturally-occurring form of the protein) and having at least about 90%, more preferably at least about 95%, and most preferably at least about 98-99% homology with a sequence of either in SEQ ID No:5-8 are also within the scope of the invention.

The present invention further pertains to recombinant forms of the subject E6AP-binding proteins which are evolutionarily related to an E6AP-binding protein represented in one of SEQ ID No:5-8, that is, not identical, yet which are capable of functioning as an agonist or an antagonist of at least one biological activity of an E6AP-binding protein. The term "evolutionarily related to", with respect to amino acid sequences of recombinant E6AP-binding proteins, refers to proteins which have amino acid sequences that have arisen naturally, as well as to mutational variants which are derived, for example, by recombinant mutagenesis.

The present invention further pertains to methods of producing the subject E6AP-binding proteins. For example, a host cell transfected with a nucleic acid vector directing expression of an E6AP-binding protein can be cultured under appropriate conditions to allow expression of the polypeptide to occur. The polypeptide may be secreted, e.g. with the use of an exogenous signal sequence, and isolated from a mixture of cells and medium containing the recombinant E6AP-BP. Alternatively, the peptide may be retained cytoplasmically, as the naturally occurring form of the protein is believed to be, and the cells harvested, lysed and the protein isolated. A cell culture includes host cells, media and other byproducts. Suitable media for cell culture are well known in the art. The recombinant E6AP-binding protein can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant E6AP-binding protein is a fusion protein containing a domain which facilitates its purification, such as a glutathione-S-transferase domain or a polyhistidine leader sequence in the form of a fusion protein with the subject polypeptides.

This invention also pertains to a host cell transfected with an E6AP-BP gene to express a recombinant form of an E6AP-binding protein. The host cell may be any prokaryotic or eukaryotic cell. Thus, a nucleotide sequence derived from the cloning of the E6AP-binding proteins of the present invention, encoding all or a selected portion of a protein, can be used to produce a recombinant form of an E6AP-BP via microbial or eukaryotic cellular processes. Ligating a polynucleotide sequence into a gene construct, such as an expression vector, and transforming or transfecting host cells with the vector are standard procedures used in producing other well-known intracellular proteins, e.g. p53, myc, cyclins and the like. Similar procedures, or modifications thereof, can be employed to prepare recombinant E6AP-binding proteins, or portions thereof, by microbial means or tissue-culture technology in accord with the subject invention. Host cells suitable for expression of a recombinant E6AP-binding protein can be selected, for example, from amongst eukaryotic (yeast, avian, insect or mammalian) or prokaryotic (bacterial) cells.

The recombinant E6AP-BP gene can be produced by ligating nucleic acid encoding an E6AP-binding protein, or a portion thereof, into a vector suitable for expression in either prokaryotic cells, eukaryotic cells, or both. Expression vectors for production of recombinant forms of E6AP-binding proteins include plasmids and other vectors. For instance, suitable vectors for the expression of an E6AP-BP include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

Preferred mammalian expression vectors contain prokaryotic sequences to facilitate the propagation of the vector in bacteria, and one or more eukaryotic transcription regulatory sequences that cause expression of a recombinant E6AP-BP gene in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found above in the description of gene therapy delivery systems.

In some instances, it may be desirable to express a recombinant E6AP-binding protein by the use of a baculovirus expression system (see, for example, *Current Protocols in Molecular Biology*, eds. Ausubel et al. John Wiley & Sons: 1992). Examples of such baculovirus expression systems include pVL-derived vectors (such as pVL1392, pVL1393 and pVL941), pAcUW-derived vectors (such as pAcUW1), and pBlueBac-derived vectors (such as the B-gal containing pBlueBac III).

The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

When expression of a portion of one of the subject E6AP-binding proteins is desired, i.e. a truncation mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751-757) and *Salmonella typhimurium* and its in vitro activity has been demonstrated on recombinant proteins (Miller et al. (1987) *PNAS* 84:2718-1722). Therefore, removal of an N-terminal methionine, if desired, can be achieved either in vivo by expressing E6AP-BP-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene. This type of expression system can be useful under conditions where it is desirable to produce an immunogenic fragment of an E6AP-binding protein. For example, the VP6 capsid protein of rotavirus can be used as an immunologic carrier protein for portions of the E6AP-BP polypeptide, either in the monomeric form or in the form of a viral particle. The nucleic acid sequences corresponding to the portion of a subject E6AP-binding protein to which antibodies are to be raised can be incorporated into a fusion gene construct which includes coding sequences for a late vaccinia virus structural protein to produce a set of recombinant viruses expressing fusion proteins comprising a portion of the protein E6AP-BP as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an E6AP-binding protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized to generate an immunogen, wherein a desired portion of a subject E6AP-binding protein is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of the subject E6AP-binding proteins can also be expressed and presented by bacterial cells.

In addition to utilizing fusion proteins to enhance immunogenicity, it is widely appreciated that fusion proteins can also facilitate the expression and purification of proteins, such as any one of the E6AP-binding proteins of the present invention. For example, an E6AP-binding protein can be generated as a glutathione-S-transferase (GST) fusion protein. Such GST fusion proteins can simplify purification of an E6AP-binding protein, as for example by affinity purification using glutathione-derivatized matrices (see, for example, *Current Protocols in Molecular Biology*, eds. Ausubel et al. (N.Y.: John Wiley & Sons, 1991)). In another embodiment, a fusion gene, coding for a purification leader sequence, such as a peptide leader sequence comprising a poly-(His)/enterokinase cleavage sequence, can be added to the N-terminus of the desired portion of an E6AP-binding protein in order to permit purification of the poly(His)-fusion protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which are subsequently annealed to generate a chimeric gene sequence (see, for example, *Current Protocols in Molecular Biology*, eds. Ausubel et al. John Wiley & Sons: 1992).

The present invention also makes available isolated E6AP-binding polypeptides which are isolated from, or otherwise substantially free of other cellular proteins, especially E6AP, p53, an E2 enzyme or other cellular macromolecules, e.g., proteins and nucleic acid, with which it might normally be associated. The term "substantially free of other cellular or viral proteins" (also referred to herein as "contaminating proteins") or "substantially pure or purified preparations" are defined as encompassing preparations of the subject polypeptides having less than 20% (by dry weight) contaminating protein, and preferably having less than 5% contaminating protein. Functional forms of the subject E6AP-binding proteins can be prepared, for the first time, as purified preparations by using recombinant proteins as described herein. Alternatively, the subject E6AP-binding proteins can be isolated by affinity purification using, for example, matrix bound E6AP protein. By "purified", it is meant, when referring to a peptide or DNA or RNA sequence, that the indicated molecule is present in the substantial absence of other biological macromolecules, such as other proteins (particularly E6AP, as well as other contaminating proteins). The term "purified" as used herein preferably means at least 80% by dry weight, more preferably in the range of 95-99% by weight, and most preferably at least 99% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

Furthermore, isolated peptidyl portions of the subject E6AP-binding proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an E6AP-binding protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of an E6AP-binding protein activity, such as by microinjection assays or in vitro protein binding assays. In an illustrative embodiment, peptidyl portions of an E6AP-binding protein, such as cln57 or cln24, can be tested for an ability to bind to E6AP by expression of the peptidyl fragments as part of thioredoxin fusion proteins, each of which contains in its active site loop a discrete fragment of the E6AP-binding protein (see, for example, U.S. Pat. Nos. 5,270,181 and 5,292,646; and PCT publication WO94/02502).

It will also be possible to modify the structure of an E6AP-binding protein for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the E6AP-binding protein described in more detail herein. Such modified peptide can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the folding of the protein, and may or may not have much of an effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine (see, for example, *Biochemistry,* 2nd ed., Ed. by L. Stryer, W H Freeman and Co.: 1981). Alternatively, amino acid replacement can be based on steric criteria, e.g. isosteric replacements, without regard for polarity or charge of amino acid sidechains. Whether a change in the amino acid sequence of a peptide results in a functional E6AP-BP homolog (e.g. functional in the sense that it acts to mimic or antagonize the wild-type form) can be readily determined by assessing the ability of the variant peptide to produce a response in cells in a fashion similar to the wild-type E6AP-BP or competitively inhibit such a response. Peptides in which more than one replacement has taken place can readily be tested in the same manner.

This invention further contemplates a method of generating sets of combinatorial mutants of the presently disclosed E6AP-binding proteins, as well as truncation and fragmentation mutants, and is especially useful for identifying potential variant sequences which are functional in binding to an E6AP protein but differ from a wild-type form of the protein by, for example, efficacy, potency and/or intracellular half-life. One purpose for screening such combinatorial libraries is, for example, to isolate novel E6AP-BP homologs which function as either an agonist or an antagonist of the biological activities of the wild-type protein, e.g., E6AP-BP homologs which inhibit p53 ubiquitination or the like, or alternatively, possess novel activities all together. To illustrate, E6AP-BP homologs can be engineered by the present method to provide proteins which bind E6AP yet prevent, e.g. inhibit, complete assembly of E6AP-dependent regulatory complexes. Such proteins, when expressed from recombinant DNA constructs, can be used in gene therapy protocols.

Likewise, mutagenesis can give rise to E6AP-BP homologs which have intracellular half-lives dramatically different than the corresponding wild-type protein. For example, the altered protein can be rendered either more stable or less stable to proteolytic degradation or other cellular process which result in destruction of, or otherwise inactivation of, an E6AP-binding protein. Such E6AP-BP homologs, and the genes which encode them, can be utilized to alter the envelope of expression for a particular recombinant E6AP-binding protein by modulating the half-life of the recombinant protein. For instance, a short half-life can give rise to more transient biological effects associated with a particular recombinant E6AP-binding protein and, when part of an inducible expression system, can allow tighter control of recombinant protein levels within a cell. As above, such proteins, and particularly their recombinant nucleic acid constructs, can be used in gene therapy protocols.

In an illustrative embodiment of this method, the amino acid sequences for a population of E6AP-BP homologs, or other related proteins are aligned, preferably to promote the highest homology possible. Such a population of variants can include, for example, E6AP-BP homologs from two or more species (orthologs), or E6AP-BP homologs from the same species but which differ due to mutation (allelic variants and paralogs). Amino acids which appear at each position of the aligned sequences are selected to create a degenerate set of combinatorial sequences. There are many ways by which the library of potential E6AP-BP homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential E6AP-BP sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules*, ed. AG Walton, Amsterdam: Elsevier pp. 273-289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386-390; Roberts et al. (1992) *PNAS* 89:2429-2433; Devlin et al. (1990) *Science* 249: 404-406; Cwirla et al. (1990) *PNAS* 87: 6378-6382, as well as U.S. Pat. Nos. 5,223,409, 5,198,346, and 5,096,815).

Alternatively, other forms of mutagenesis can be utilized to generate a combinatorial library, particularly where no other naturally occurring homologs have yet been sequenced. For example, E6AP-BP homologs (both agonist and antagonist forms) can be generated and isolated from a library by screening using, for example, alanine scanning mutagenesis and the like (Ruf et al. (1994) *Biochemistry* 33:1565-1572; Wang et al. (1994) *J. Biol. Chem.* 269:3095-3099; Balint et al. (1993) *Gene* 137:109-118; Grodberg et al. (1993) *Eur. J. Biochem.* 218:597-601; Nagashima et al. (1993) *J. Biol. Chem.* 268: 2888-2892; Lowman et al. (1991) *Biochemistry* 30:10832-10838; and Cunningham et al. (1989) *Science* 244:1081-1085), by linker scanning mutagenesis (Gustin et al. (1993) *Virology* 193:653-660; Brown et al. (1992) *Mol. Cell. Biol.* 12:2644-2652; McKnight et al. (1982) *Science* 232:316); by saturation mutagenesis (Meyers et al. (1986) *Science* 232: 613); by PCR mutagenesis (Leung et al. (1989) *Method Cell Mol Biol* 1:11-19); or by random mutagenesis (Miller et al. (1992) *A Short Course in Bacterial Genetics*, CSHL Press, Cold Spring Harbor, N.Y.; and Greener et al. (1994) *Strategies in Mol Biol* 7:32-34).

A wide range of techniques are known in the art for screening gene products of combinatorial libraries made by point mutations, as well as for screening cDNA libraries for gene products having a certain property. Such techniques will be generally adaptable for rapid screening of the gene libraries generated by the combinatorial mutagenesis of E6AP-binding proteins. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate E6AP-BP sequences created by combinatorial mutagenesis techniques.

In one screening assay, the candidate gene products are displayed on the surface of a cell or viral particle, and the ability of particular cells or viral particles to bind an E6AP protein via this gene product is detected in a "panning assay". For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370-1371; and Goward et al. (1992) *TIBS* 18:136-140). In a similar fashion, fluorescently labeled E6AP can be used to score for potentially functional E6AP-BP homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd., and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007-16010; Griffiths et al. (1993) *EMBO J* 12:725-734; Clackson et al. (1991) *Nature* 352:624-628; and Barbas et al. (1992) *PNAS* 89:4457-4461). In an illustrative embodiment, the recombinant phage antibody system (RPAS, Pharmacia Catalog number 27-9400-01) can be easily modified for use in expressing and E6AP-BP combinatorial libraries, and the E6AP-BP phage library can be panned on glutathione immobilized E6AP-GST fusion proteins. Successive rounds of phage amplification and panning can greatly enrich for E6AP-BP homologs which retain an ability to bind E6AP and which can subsequently be screened for further biological activities in order to discern between agonists and antagonists.

In yet another illustrative embodiment, the p53-dependent reporter construct described in U.S. Ser. No. 08/176,937, now abandoned, can be used to identify antagonists through their ability to enhance expression of the reporter gene by inhibiting the degradation of p53 by the action of the wild-type E6AP-binding protein. Thus, a combinatorial library can screened by a detecting expression of the reporter gene, and appropriate clones isolated for further manipulation.

Other forms of mutagenesis can also be utilized to generate a combinatorial library from the subject E6AP-binding proteins. For example, E6AP-BP homologs (both agonist and antagonist forms) can be generated and isolated from a library by screening using, for example, alanine scanning mutagenesis and the like (Ruf et al. (1994) *Biochemistry* 33:1565-1572; Wang et al. (1994) *J. Biol. Chem.* 269:3095-3099; Balint et al. (1993) *Gene* 137:109-118; Grodberg et al. (1993) *Eur. J. Biochem.* 218:597-601; Nagashima et al. (1993) *J. Biol. Chem.* 268:2888-2892; Lowman et al. (1991) *Biochemistry* 30:10832-10838; and Cunningham et al. (1989) *Science* 244:1081-1085), by linker scanning mutagenesis (Gustin et al. (1993) *Virology* 193:653-660; Brown et al. (1992) *Mol. Cell. Biol.* 12:2644-2652; McKnight et al. (1982) *Science* 232:316); by saturation mutagenesis (Meyers et al. (1986) *Science* 232:613); by PCR mutagenesis (Leung et al. (1989) *Method Cell Mol Biol* 1:11-19); or by random mutagenesis (Miller et al. (1992) *A Short Course in Bacterial Genetics*, CSHL Press, Cold Spring Harbor, N.Y.; and Greener et al. (1994) *Strategies in Mol Biol* 7:32-34).

The invention also provides for reduction of the E6AP-binding domains of the subject protein to generate mimetics, e.g. peptide or non-peptide agents, which are able to disrupt binding of a polypeptide of the present invention with an E6AP protein. Thus, such mutagenic techniques as described above are also useful to map the determinants of E6AP-binding proteins which participate in protein-protein interactions involved in, for example, binding of an E6AP-BP to other proteins of a ubiquitin-conjugating system (both cellular and viral), as well as (if applicable) ubiquitin substrates such as p53. To illustrate, the critical residues of an E6AP-binding protein which are involved in molecular recognition of E6AP can be determined and used to generate E6AP-BP-derived peptidomimetics that competitively inhibit binding of the E6AP-BP to E6AP. By employing, for example, scanning mutagenesis to map the amino acid residues of a particular E6AP-binding protein involved in binding E6AP, peptidomimetic compounds can be generated which mimic those residues in binding to E6AP, and which, by inhibiting binding of the E6AP-BP to E6AP, can interfere with the function of E6AP in regulating the half-life of cell cycle regulatory proteins, e.g., p53, cyclins, or p27. For instance, non-hydrolyzable peptide analogs of such residues can be generated using retro-inverse peptides (e.g., see U.S. Pat. Nos. 5,116,947 and 5,218,089; and Pallai et al. (1983) *Int J Pept Protein Res* 21:84-92) benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides. Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71). Such peptidomimetics can serve as drugs which prevent the action of E6AP or an E6AP-binding protein.

Another aspect of the invention pertains to an antibody specifically reactive with one of the subject E6AP-binding proteins. For example, by using immunogens derived from an E6AP-binding protein, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., a full length E6AP-binding protein or an antigenic fragment which is capable of eliciting an antibody response). Techniques for conferring immunogenicity on a protein or peptide include conjugation to carriers or other techniques well known in the art. An immunogenic portion of one of the subject E6AP-binding proteins can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the E6AP-binding proteins of the present invention, e.g. antigenic determinants of a protein represented in one of SEQ ID Nos:5-8 or a closely related human or non-human mammalian homolog thereof. For instance, a favored anti-E6AP-BP antibody of the present invention does not substantially cross react (i.e. react specifically) with a protein which is less than 90 percent homologous to one of SEQ ID Nos:5-8; though antibodies which do not substantially cross react with a protein which is less than 95 percent homologous with one of SEQ ID Nos:5-8, or even less than 98-99 percent homologous with one of SEQ ID Nos:5-8, are specifically contemplated. By "not substantially cross react", it is meant that the antibody has a binding affinity for a non-homologous protein (e.g. E6AP) which is at least one order of magnitude, more preferably at least two orders of magnitude, and even more preferably at least three orders of magnitude less than the binding affinity for a protein represented one of SEQ ID Nos:5-8.

Following immunization, anti-E6AP-BP antisera can be obtained and, if desired, polyclonal anti-E6AP-BP antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature,* 256: 495-497), the human B cell hybridoma technique (Kozbar et al., (1983) *Immunology Today,* 4: 72), and the EBV-hybridoma technique to produce human monoclonal antibodies (Cole et al., (1985) *Monoclonal Antibodies and Cancer Therapy*, Alan R. Liss, Inc. pp. 77-96). Hybridoma cells can be screened immunochemically for production of antibodies specifically reactive with an E6AP-binding protein of the present invention and monoclonal antibodies isolated from a culture comprising such hybridoma cells.

The term antibody as used herein is intended to include fragments thereof which are also specifically reactive with one of the subject E6AP-binding protein. Antibodies can be fragmented using conventional techniques, including recombinant engineering, and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments. The antibody of the present invention is further intended to include bispecific and chimeric molecules having an anti-E6AP-BP portion.

Both monoclonal and polyclonal antibodies (Ab) directed against an E6AP-binding protein can be used to block the action of that protein and allow the study of the role of a particular E6AP-binding protein in cell cycle or cell proliferation.

Antibodies which specifically bind E6AP-BP epitopes can also be used in immunohistochemical staining of tissue samples in order to evaluate the abundance and pattern of expression of each of the subject E6AP-binding proteins. Anti-E6AP-BP antibodies can be used diagnostically in immuno-precipitation and immuno-blotting to detect and evaluate E6AP-BP levels in tissue or bodily fluid as part of a clinical testing procedure. For instance, such measurements as the level of E6AP-BP/E6AP complexes can be useful in predictive valuations of the onset or progression of tumors. Likewise, the ability to monitor E6AP-BP levels in the cells of an individual can permit determination of the efficacy of a given treatment regimen for an individual afflicted with such a disorder. The level of an E6AP-binding protein can be measured in cells found in bodily fluid, such as in samples of cerebral spinal fluid, or can be measured in tissue, such as produced by biopsy. Diagnostic assays using anti-E6AP-BP antibodies can include, for example, immunoassays designed to aid in early diagnosis of a neoplastic or hyperplastic disorder, e.g., the presence of cancerous cells in the sample, e.g., to detect cells in which a lesion of the E6AP-BP gene has occurred or in which the protein is misexpressed or found in abnormal protein complexes.

Another application of the subject antibodies is in the immunological screening of cDNA libraries constructed in expression vectors such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of an E6AP-binding protein can then be detected with antibodies, as, for example, reacting nitrocellulose filters lifted from infected plates with anti-E6AP-BP antibodies. Phage, scored by this assay, can then be isolated from the infected plate. Thus, the presence of E6AP-BP homologs can be detected and cloned from other animals, and alternate isoforms (including splicing variants) can be detected and cloned from human sources.

Moreover, the nucleotide sequence determined from the cloning of the subject E6AP-binding proteins from a human cell line will further allow for the generation of probes designed for use in identifying homologs in other human cell types, as well as E6AP-BP homologs (e.g. orthologs) from other animals. For instance, the present invention also provides a probe/primer comprising a substantially purified oligonucleotide, which oligonucleotide comprises a region of nucleotide sequence that hybridizes under stringent conditions to at least 10 consecutive nucleotides of sense or antisense sequence of one of SEQ ID Nos: 1-4, or naturally occurring mutants thereof. In preferred embodiments, the probe/primer further comprises a label group attached thereto and able to be detected, e.g. the label group is selected from the group consisting of radioisotopes, fluorescent compounds, enzymes, and enzyme co-factors. Such probes can also be used as a part of a diagnostic test kit for identifying transformed cells, such as for measuring a level of an E6AP-BP nucleic acid in a sample of cells from a patient; e.g. detecting mRNA encoding an E6AP-BP mRNA level; e.g. determining whether a genomic E6AP-BP gene has been mutated or deleted.

In addition, nucleotide probes can be generated which allow for histological screening of intact tissue and tissue samples for the presence of an E6AP-BP mRNA. Similar to the diagnostic uses of anti-E6AP-BP antibodies, the use of probes directed to E6AP-BP mRNAs, or to genomic E6AP-BP sequences, can be used for both predictive and therapeutic evaluation of allelic mutations which might be manifest in, for example, neoplastic or hyperplastic disorders (e.g. unwanted cell growth). Used in conjunction with an antibody immunoassays, the nucleotide probes can help facilitate the determination of the molecular basis for a developmental disorder which may involve some abnormality associated with expression (or lack thereof) of an E6AP-binding protein. For instance, variation in synthesis of an E6AP-binding protein can be distinguished from a mutation in the genes coding sequence.

Accordingly, the present method provides a method for determining if a subject is at risk for a disorder characterized by unwanted cell proliferation. In preferred embodiments, the subject method can be generally characterized as comprising detecting, in a tissue sample of the subject (e.g. a human patient), the presence or absence of a genetic lesion characterized by at least one of (i) a mutation of a gene encoding one of the subject E6AP-binding proteins or (ii) the mis-expression of an E6AP-BP gene. To illustrate, such genetic lesions can be detected by ascertaining the existence of at least one of (i) a deletion of one or more nucleotides from an E6AP-BP gene, (ii) an addition of one or more nucleotides to such an E6AP-BP gene, (iii) a substitution of one or more nucleotides of an E6AP-BP gene, (iv) a gross chromosomal rearrangement of one of the E6AP-BP genes, (v) a gross alteration in the level of a messenger RNA transcript of an E6AP-BP gene, (vi) the presence of a non-wild type splicing pattern of a messenger RNA transcript of an E6AP-BP gene, and (vii) a non-wild type level of an E6AP-binding protein. In one aspect of the invention there is provided a probe/primer comprising an oligonucleotide containing a region of nucleotide sequence which is capable of hybridizing to a sense or antisense sequence of one of SEQ ID Nos: 1-4, or naturally occurring mutants thereof, or 5' or 3' flanking sequences or intronic sequences naturally associated with the subject E6AP-BP genes. The probe is exposed to nucleic acid of a tissue sample; and the hybridization of the probe to the sample nucleic acid is detected. In certain embodiments, detection of the lesion comprises utilizing the probe/primer in a polymerase chain reaction (PCR) (see, e.g., U.S. Pat. Nos. 4,683,195 and 4,683,202) or, alternatively, in a ligation chain reaction (LCR) (see, e.g., Landegran et al. (1988) *Science*, 241:1077-1080; and NaKazawa et al. (1944) *PNAS* 91:360-364) the later of which can be particularly useful for detecting point mutations in the E6AP-BP gene. Alternatively, immunoassays can be employed to determine the level of E6AP-binding protein and/or its participation in protein complexes, particularly transcriptional regulatory complexes such as those involving E6AP.

Furthermore, by making available purified and recombinant E6AP-binding proteins, the present invention facilitates the development of assays which can be used to screen for drugs which are either agonists or antagonists of the cellular function of each of the subject E6AP-binding proteins, or of their role in the pathogenesis of proliferative and differentiative disorders. For instance, an assay can be generated according to the present invention which evaluates the ability of a compound to modulate binding between an E6AP-binding protein and an E6AP protein. A variety of assay formats will suffice and, in light of the present invention, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target when contacted with a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. In one embodiment, the drug screening assays can be generated to detect inhibitory agents on the basis of their ability to interfere with binding of E6AP-BP and any other immediate upstream or downstream component of the ubiquitin conjugation pathway. In an exemplary screening assay of the present invention, the compound of interest is contacted with a mixture generated from an isolated and purified E6AP-binding protein, such as cln57 or cln24, and another component of the ubiquitin conjugation pathway which binds to E6AP-BP (e.g. an E6AP), or other cellular substrates of E6AP-BP. Detection and quantification of E6AP/E6AP-BP complexes provides a means for determining the compound's efficacy at inhibiting (or potentiating) complex formation between the E6AP protein and the E6AP-binding protein. The efficacy of the compound can be assessed by generating dose response curves from data obtained using various concentrations of the test compound. Moreover, a control assay can also be performed to provide a baseline for comparison. In the control assay, isolated and purified E6AP-BP is added to a composition containing the E6AP protein, and the formation of E6AP/E6AP-BP complex is quantitated in the absence of the test compound.

Complex formation between the E6AP-binding protein and an E6AP may be detected by a variety of techniques. For instance, modulation in the formation of complexes can be quantitated using, for example, detectably labelled proteins (e.g. radiolabelled, fluorescently labelled, or enzymatically labelled), by immunoassay, or by chromatographic detection.

Typically, it will be desirable to immobilize either the E6AP protein or the E6AP-binding protein to facilitate separation of E6AP/E6AP-BP complexes from uncomplexed forms of one of the proteins, as well as to accommodate automation of the assay. In an illustrative embodiment, a fusion protein can be provided which adds a domain that permits the protein to be bound to an insoluble matrix. For example, glutathione-S-transferase/E6AP (GST/E6AP) fusion proteins can be adsorbed onto glutathione sepharose beads (Sigma Chemical, St. Louis, Mo.) or glutathione derivatized microtitre plates, which are then combined with the E6AP-binding protein, e.g. an $^{35}$S-labeled E6AP-binding protein, and the test compound and incubated under conditions conducive to complex formation. Following incubation, the beads are washed to remove any unbound E6AP-BP, and the matrix bead-bound radiolabel determined directly (e.g. beads placed in scintilant), or in the superntantant after the E6AP/E6AP-BP complexes are dissociated, e.g. when microtitre plates is used. Alternatively, after washing away unbound protein, the complexes can be dissociated from the matrix, separated by SDS-PAGE gel, and the level of E6AP-BP found in the matrix-bound fraction quantitated from the gel using standard electrophoretic techniques.

Other techniques for immobilizing proteins on matrices are also available for use in the subject assay. For instance, the E6AP protein can be immobilized utilizing conjugation of biotin and streptavidin. For instance, biotinylated E6AP can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with E6AP can be derivatized to the wells of the plate, and E6AP trapped in the wells by antibody conjugation. As above, preparations of an E6AP-binding protein and a test compound are incubated in the E6AP-presenting wells of the plate, and the amount of E6AP/E6AP-BP complex trapped in the well can be quantitated. Exemplary methods for detecting such complexes, in addition to those described above for the GST-immobilized complexes, include immunodetection of complexes using antibodies reactive with the E6AP-binding protein, or which are reactive with the E6AP protein and compete for binding with the E6AP-BP; as well as enzyme-linked assays which rely on detecting an enzymatic activity associated with the E6AP-binding protein. In the instance of the latter, the enzyme can be chemically conjugated or provided as a fusion protein with the E6AP-binding protein. To illustrate, the E6AP-binding protein can be chemically cross-linked with alkaline phosphatase, and the amount of E6AP-BP trapped in the complex can be assessed with a chromogenic substrate of the enzyme, e.g. paranitrophenyl phosphate. Likewise, a fusion protein comprising the E6AP-BP and glutathione-S-transferase can be provided, and complex formation quantitated by detecting the GST activity using 1-chloro-2,4-dinitrobenzene (Habig et al (1974) *J Biol Chem* 249:7130).

For processes which rely on immunodetection for quantitating one of the proteins trapped in the complex, antibodies against the protein, such as the anti-E6AP-BP antibodies described herein, can be used. Alternatively, the protein to be detected in the complex can be "epitope tagged" in the form of a fusion protein which includes, in addition to the E6AP-BP or E6AP sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150-21157) which includes a 10-residue sequence from c-myc, as well as the pFLAG system (International Biotechnologies, Inc.) or the pEZZ-protein A system (Pharamacia, N.J.).

Additionally, the subject E6AP-binding proteins can be used to generate an interaction trap assay, as described in the examples below (see also, U.S. Pat. No. 5,283,317; PCT publication WO94/10300; Zervos et al. (1993) *Cell* 72:223-232; Madura et al. (1993) *J Biol Chem* 268:12046-12054; Bartel et al. (1993) *Biotechniques* 14:920-924; and Iwabuchi et al. (1993) *Oncogene* 8:1693-1696), for detecting agents which either potentiate or attenuate complex formation between an E6AP-binding protein and E6AP. As described below, the interaction trap assay relies on reconstituting in vivo a functional transcriptional activator protein from two separate fusion proteins, one of which comprises the DNA-binding domain of a transcriptional activator fused to an E6AP protein. The second fusion protein comprises a transcriptional activation domain (e.g. able to initiate RNA polymerase transcription) fused to one of the subject E6AP-binding proteins. When the E6AP and E6AP-binding protein interact, the two domains of the transcriptional activator protein are brought into sufficient proximity as to cause transcription of a reporter gene. In addition to the LexA interaction trap described in the examples below, yet another illustrative embodiment comprises *Saccharomyces cerevisiae* YPB2 cells transformed simultaneously with a plasmid encoding a GAL4 db-E6AP fusion (db: DNA binding domain) and with a plasmid encoding the GAL4 activation domain (GAL4ad) fused to a subject E6AP-BP. Moreover, the strain is transformed such that the GAL4-responsive promoter drives expression of a phenotypic marker. For example, the ability to grow in the absence of histidine can depends on the expression of the HIS3 gene. When the HIS3 gene is placed under the control of a GAL4-responsive promoter, relief of this auxotrophic phenotype indicates that a functional GAL4 activator has been reconstituted through the interaction of E6AP and the E6AP-BP. Thus, agent able to inhibit E6AP-BP interaction with E6AP will result in yeast cells unable to growth in the absence of histidine. Alternatively, the phenotypic marker (e.g. instead of the HIS3 gene) can be one which provides a negative selection when expressed such that agents which disrupt E6AP/E6AP-BP interactions confer positive growth selection to the cells. Commercial kits which can be modified to develop two-hybrid assays with the subject E6AP-binding proteins are presently available (e.g., MATCHMAKER kit, ClonTech catalog number K1605-1, Palo Alto, Calif.).

In yet another embodiment of the subject assays, the system is derived to detect the effect of a test agent on an E6AP-BP dependent ubiquitination reaction. Assays for the measurement of ubiquitination can be generated in many different forms, and include assays based on cell-free systems, e.g.

purified proteins or cell lysates, as well as cell-based assays which utilize intact cells. Assays as described herein can be used in conjunction with the subject E6AP-binding protein to generate a ubiquitin-conjugating system for detecting agents able to inhibit E6AP-BP mediated ubiquitination of a cellular or viral regulatory proteins.

Accordingly, potential inhibitors of E6AP-BP function can be detected in a cell-free assay generated by constitution of a functional ubiquitin-protein ligase system in a cell lysate, such as generated by charging a ubiquitin-depleted reticulocyte lysate (Hersko et al. (1983) *J Biol Chem* 258:8206-6214) with, in addition to E6AP-BP and as needed, an E1 enzyme, ubiquitin, and a substrate for E6AP-BP dependent ubiquitination (e.g. a "target protein"). The level of ubiquitination of the target protein can be determined by quantitating the amount of ubiquitin conjugated to the protein, and is determined in the presence and absence of a test compound. A statistically significant decrease in ubiquitination of the target protein in the presence of the test compound is indicative of the test compound being an inhibitor of E6AP-BP dependent ubiquitin conjugation, with background activity from other E3 enzymes in the lysate being controlled for by performing the same assay without exogenous E6AP-BP. It will be understood that the "target protein" can be a cellular or viral protein, such as though regulatory proteins described herein, or it could be E6AP-BP itself.

Ubiquitination of the target protein via an in vitro ubiquitin-conjugating system, in the presence and absence of a candidate inhibitor, can be accomplished in any vessel suitable for containing the reactants. Examples include microtitre plates, test tubes, and micro-centrifuge tubes. In certain embodiments of the present assay, the in vitro assay system is generated to lack the ability to degrade the ubiquitinated target protein, such as by addition of protease inhibitors to the lysate. In such an embodiments, a wide range of detection means can be practiced to score for the presence of a ubiquitinated protein.

In one embodiment of the present assay, the products of a non-degradative ubiquitin-conjugating system are separated by gel electrophoresis, and the level of ubiquitinated target protein assessed, using standard electrophaesis protocols, by measuring an increase in molecular weight of the target protein that corresponds to the addition of one or more ubiquitin chains. For example, one or both of the target protein and ubiquitin can be labeled with a radioisotope such as $^{35}S$, $^{14}C$, or $^{3}H$, and the isotopically labeled protein bands quantified by autoradiographic techniques. Standardization of the assay samples can be accomplished, for instance, by adding known quantities of labeled proteins which are not themselves subject to ubiquitination or degradation under the conditions which the assay is performed. Similarly, other means of detecting electrophoretically separated proteins can be employed to quantify the level of ubiquitination of the target protein, including immunoblot analysis using antibodies specific for either the target protein or ubiquitin, or derivatives thereof. As described below, the antibody can be replaced with another molecule able to bind one of either the target protein or ubiquitin. By way of illustration, one embodiment of the present assay comprises the use of biotinylated ubiquitin in the conjugating system. The biotin label is detected in a gel during a subsequent detection step by contacting the electrophoretic products (or a blot thereof) with a streptavidin-conjugated label, such as a streptavidin linked fluorochrome or enzyme, which can be readily detected by conventional techniques. Moreover, where a reconstituted protein mixture is used (rather than a lysate) as the conjugating system, it may be possible to simply detect the target protein and ubiquitin conjugates in the gel by standard staining protocols, including coomassie blue and silver staining.

In another embodiment, an immunoassay or similar binding assay, is used to detect and quantify the level of ubiquitinated protein produced in the ubiquitin-conjugating system. Many different immunoassay techniques are amenable for such use and can be employed to detect and quantitate the target protein:Ub conjugates. For example, the wells of a microtitre plate (or other suitable solid phase) can be coated with an antibody which specifically binds one of either the target protein or ubiquitin. After incubation of the ubiquitin-conjugating system with and without the candidate agent, the products are contacted with the matrix bound antibody, unbound material removed by washing, and ubiquitin conjugates of the target protein specifically detected. To illustrate, if an antibody which binds the target protein can be used to sequester the protein on the matrix, then a detectable anti-ubiquitin antibody can be used to score for the presence of ubiquitinated target protein on the matrix.

However, it will be clear to those skilled in the art that the use of antibodies in these binding assays is merely illustrative of binding molecules in general, and that the antibodies are readily substituted in the assay with any suitable molecule that can specifically detect one of either the target protein or the ubiquitin. For instance, a biotin-derivative of ubiquitin can be used, and streptavidin (or avidin) employed to bind the biotinylated ubiquitin. In an illustrative embodiment, wells of a microtitre plate are coated with streptavidin and contacted with the developed ubiquitin-conjugating system under conditions wherein the biotinylated ubiquitin binds to and is sequestered in the wells. Unbound material is washed from the wells, and the level of target protein (bound to the matrix via a conjugated ubiquitin moiety) is detected in each well. Alternatively, the microtitre plate wells can be coated with an antibody (or other binding molecule) which binds and sequesters the target protein on the solid support, and detection of ubiquitinated conjugates of the matrix-bound target protein are subsequently carried out using a detectable streptavidin derivative, such as an alkaline phosphatase/streptavidin complex.

In similar fashion, epitope-tagged ubiquitin, such as myc-ub (see Ellison et al. (1991) *J. Biol. Chem.* 266:21150-21157; ubiquitin which includes a 10-residue sequence encoding a protein of c-myc) can be used in conjunction with antibodies to the epitope tag. A major advantage of using such an epitope-tagged ubiquitin approach for detecting Ub:protein conjugates is the ability of an N-terminal tag sequences to inhibit ubiquitin-mediated proteolysis of the conjugated target protein.

Other ubiquitin derivatives include detectable labels which do not interfere greatly with the conjugation of ubiquitin to the target protein. Such detectable lables can include fluorescently-labeled (e.g. FITC) or enzymatically-labeled ubiquitin fusion proteins. These derivatives can be produced by chemical cross-linking, or, where the label is a protein, by generation of a fusion protein. Several labeled ubiquitin derivatives are commercially available.

Likewise, other binding molecules can be employed in place of the antibodies that bind the target protein. For example, the target protein can be generated as a glutathione-S-transferase (GST) fusion protein as described above. Glutathione derivatized matrices (e.g. glutathione-sepharose or glutathione-coated microtitre plates) can be used to sequester free and ubiquitinated forms of the target protein from the ubiguitin-conjugating system, and the level of ubiquitin immobilized can be measured as described. Likewise, where the matrix can be generated to bind ubiquitin, and the level of sequestered GST-target protein can be detected using agents which bind to the GST moiety (such as anti-GST antibodies), or, alternatively, using agents which are enzymatically acted upon by GST to produce detectable products (e.g. 1-chloro-2,4-dinitrobenzene; Habig et al. (1974) *J Biol Chem* 249: 7130). Similarly, other fusion proteins involving the target protein and an enzymatic activity are contemplated by the present method. For example, fusion proteins containing β-galactosidase or luciferase, to name but a few, can be employed as labels to determine the amount of target protein sequestered on a matrix by virtue of a conjugated ubiquitin chain.

Moreover, such enzymatic fusion proteins can be used to detect and quantitate ubiquitinated target protein in a heterogeneous assay, that is one which does not require separation of the components of the conjugating system. For example, ubiquitin conjugating lysates can be generated to have a ubiquitin-dependent protease which degrades the target protein. The enzymatic activity of the fusion protein provides a detectable signal, in the presence of substrate, for measuring the level of the target protein ubiquitination. Similarly, in a non-degradative conjugating system, ubiquitination of the target protein portion of the fusion protein can allosterically influence the enzymatic activity associated with the fusion the protein and thereby provides a means for monitoring the level of ubiquitin conjugation.

As additional guidance for carrying out such assays, it is noted that ubiquitin is available from commercial sources (Bovine ubiquitin, Sigma catalog no. 6253; yeast ubiquitin, Sigma catalog no. 2129), as are various modified forms of ubiquitin, as for example, fluorescein-labeled ubiquitin (Sigma catalog no. U5504), and horseradish-peroxidase labeled ubiquitin (Sigma catalog no. U9879). Biotinylated ubiquitin can be prepared from biotin-NHS(N-hydroxy-succinimide ester) using well-known techniques (biotinylation kit; Pierce catalog no. 214206, 203188 (6 atom spacer), or 203114 (14 atom spacer)). For generating certain of the detection means as described herein, some of the following reagents can be employed: polyclonal sera to ubiquitin (Sigma catalog no. U5379); labeled antibodies to biotin (Sigma catalog nos. A4541 (peroxidase conjugated) and F6762 (FITC conjugated)); labeled avidin (Sigma catalog nos. A7294, E2636 (peroxidase conjugated) and A2050, E2761 (FITC conjugated)); streptavidin (Sigma catalog no. S3762 (FITC conjugated) and S5512 (peroxidase conjugated)); Streptavidin-coated beads (Sigma catalog no. 400996; Pierce catalog no. 20347G); Streptavidin-coated 96 well microtiter plates (Pierce catalog no. 15124); Maleic anhydride-activated polystyrene 96 well plates (Pierce catalog no. 15110); and antibodies to human p53 (PharMingen catalog Nos. 14091A and 14211A), human c-myc (PharMingen catalog Nos. 14861A and 14851A), and human cyclins (PharMingen Catalog Nos: 14531A, 14541A, 14551A, 14561A, 14821A, 14781A, and 14491A). Reticulocyte lysates suitable for use in the present assay have been previously described (see, for example, Berleth et al. (1992) *J Biol Chem* 267:16405-16411; Scheffner et al. (1990) *Cell* 63:1129-1136; Scheffner et al. (1992) *EMBO J* 11:2425-2431; and Hershko et al. (1983) J Biol Chem 258:8206-8214), as have been methods for isolating components of the ubiquitin conjugating system (e.g. Hershko et al., supra; and Scheffner et al. (1993) *Cell* 75:495-505, describing E1 and E6/E6-AP isolation).

In one embodiment of the invention, the target regulatory protein is the tumor suppressor p53, and any one of the above assays is used to identify inhibitors of ubiquitin-mediated destruction of p53, such as agents which act by disrupting interaction of an E6AP-BP and other proteins of the ubiquitin system, such as E6AP.

The p53 gene is a known tumor-suppressing gene (Green (1989) *Cell* 56:1-3; Mowat et al (1985 *Nature* 314:633-636). The protein encoded by the p53 gene is a nuclear protein that forms a stable complex with both the SV40 large T antigen and the adenovirus E1B 55 kd protein. The p53 gene product may be inactivated by binding to these proteins. Many lines of evidence point to the importance of p53 in human carcinogenesis. For instance, mutations within the p53 gene are the most frequent genetic aberration thus far associated with human cancer. Emerging evidence suggests that p53 is a checkpoint protein that plays an important role in sensing DNA damage or regulating cellular response to stress.

Under normal conditions, p53 is an unstable protein and is present at very low levels in the cell. The level of p53 in a cell appears to be controlled at least in party by degradation involving the ubiquitin system. Treating cells with UV light or X rays dramatically reduces the rate of p53 degradation, leading to a rapid increase in its concentration in the cell and presumably inducing the transcription of genes that block passage through the restriction point. However, while normal cell lines irradiated in G1 fail to enter S phase, many tumor cell lines do not. In fact, there is a perfect correlation between cell lines that lack this feedback control and cells that have mutations in the p53 gene. These mutations are of two sorts: recessive mutations that inactivate the gene, and dominant mutations that produce abnormal proteins.

An inhibitor developed to modulate the bioactivity of one of the subject E6AP-BP may be useful therapeutically to enhance the function of the p53 checkpoint by increasing the steady state concentration of p53 in the treated cell. It will be apparent that the subject compositions and assays can be used to derive pharmaceutical preparations for controlling the proliferation of tissue, such as epithelial-derived tissue, as in the treatment of disorders marked by aberrant proliferation, or in the repair of damaged tissue. For example, the control of ubiquitination of p53 can be used in the treatment of disorders, or surgical or cosmetic repair of such epithelial tissues as skin and skin organs; corneal, lens and other ocular tissue; mucosal membranes; and periodontal epithelium. For instance, the compositions disclosed herein provide for the treatment or prevention of a variety of damaged epitheiial and mucosal tissues, particularly those resulting from hyperplastic or neoplastic conditions, especially those having a papillomavirus as a causative agent. For instance, it will be evident that the such compositions will find ready application for the treatment or prophylaxis of, for example, psoriasis; keratosis; acne; comedogenic lesions; verrucous lesions such as verruca plana, plantar warts, verruca acuminata, and other verruciform lesions marked by proliferation of epithelial cells; folliculitis and pseudofolliculitis; keratoacanthoma; callosities; Darier's disease; ichthyosis; lichen planus; molluscous contagiosum; melasma; Fordyce disease; and keloids or hypertrophic scars. For example, certain of the E6AP-BP antisense formulations of the present invention may also be used as part of treatment regimens in auto-immune diseases for affecting healing of proliferative manifestations of the disorder, as for example, part of a treatment for aphthous ulcers, pemphigus such as pemphigus vulgaris, pemphigus foliaceus, pemphigus vegetans or pemphigus erythematous, epidermolysis, lupus lesions or desquamative lesions.

Furthermore, the subject method can be used to control wound healing processes, as for example may be desirable in connection with any surgery involving epithelial tissue, such as from dermatological or periodontal surgeries. Exemplary surgical repair for which E6AP-BP antisense therapy, for example, is a candidate treatment include severe burn and skin regeneration, skin grafts, pressure sores, diabetic ulcers, fissures, post surgery scar reduction, and ulcerative colitis.

The subject compositions can also be employed to cause inhibition of hair growth, as for example, a way of reducing the growth of human hair as opposed to its conventional removal by cutting, shaving, or depilation, e.g. in the treatment of trichosis, as well as to protect hair follicle cells from radiation-induced death during cytotoxic therapies.

Moreover, the oncogenic activity of certain viruses, such as the simian virus 40 (SV40), the adenovirus type 5 (Ad5), and the high human papilloma virus types 16 and 18 (HPV16 and HPV18), has been correlated with the virus' ability to interact with and inactivate the cellular p53 protein. In the instance of the high-risk papilloma viruses, the association of the viral oncoprotein E6 with p53 leads to the specific ubiquitination and degradation of p53. This has suggested a model in which E6 immortalizes cells by deregulating cell growth control through the elimination of the p53 tumor suppressor protein. This models accounts for the observations that p53 levels are very low in HPV-immortalized cells and that the half-life of p53 in HPV16-immortalized keratinocytes is shorter than in primary keratinocytes. Thus, the present invention can be employed in the identification of an agent that can block the ubiquitin dependent degradation of p53 as mediated by E6, and thereby block proliferation of HPV-transformed cells.

Moreover, the oncogenic activity of certain viruses, such as the simian virus 40 (SV40), the adenovirus type 5 (Ad5), and the high human papilloma virus types 16 and 18 (HPV16 and HPV18), has been correlated with the virus' ability to interact with and inactivate the cellular p53 protein. In the instance of the high-risk papilloma viruses, the association of the viral oncoprotein E6 with p53 leads to the specific ubiquitination and degradation of p53. This has suggested a model in which E6 immortalizes cells by deregulating cell growth control through the elimination of the p53 tumor suppressor protein. This models accounts for the observations that p53 levels are very low in HPV-immortalized cells and that the half-life of p53 in HPV16-immortalized keratinocytes is shorter than in primary keratinocytes. Thus, the present invention can be employed in the identification of an agent that can block the ubiquitin dependent degradation of p53 as mediated by E6, and thereby block proliferation of HPV-transformed cells.

The subject E6AP-BP is likely to be involved in altering the activity of other cellular proteins, particularly proteins which seem to have short half-lives, and the present invention contemplates the use of E6AP-BP inhibitors, including antagonistic forms of the E6AP-binding protein, to inhibit the ubiquitination of other cellular proteins by E6AP-BP. For example, in another embodiment, the regulatory protein ubiquitinated by E6AP-BP is the myc oncoprotein. The myc regulatory protein is activated by translocation or mutation in many B-cell lymphomas or by amplification in tumor types, such as small cell lung cancer and breast cancer. The c-myc gene is the cellular homolog of the viral oncogene v-myc, which is found in a number of avian and feline retroviruses which induce leukemia and carcinomas. Myc has been implicated in the control of normal cell proliferation by many studies. In particular, it is one of the immediate early growth response genes that are rapidly induced in quiescent cells upon mitogenic induction, suggesting that it plays some role in mediating the transition from quiescence to proliferation. However, increased levels of myc itself is not sufficient to cause proliferation. In fact, in normal cells the opposite happens and the cell undergoes apoptosis. Therefore, inhibitors identified in the present assay can be used to effectively induce apoptosis in cells which do not normally overexpress myc. For example, specific delivery of these agents to lymphocytes can be used to inhibit proliferation of B- and/or T-cells in order to induce clonal deletion and generate tolerance to particular antigens.

In preferred embodiments the subject composition is preferably capable of: suppressing tumor growth, e.g., in a tumor cell in which the endogenous E6AP-binding protein is involved in p53 regulation; suppressing growth of papillomavirus-infected cells, e.g., HPV-infected cells; inhibiting growth of a papillomavirus-infected cell, e.g., an HPV-infected cell, e.g., a high-risk HPV infected cell, e.g., and HPV-16, -18, -31, or -33 infected cell, e.g., a bovine papillomavirus (BPV)-infected cell; inhibiting infection of a cell by a papillomavirus, e.g., an HPV, e.g., a high-risk HPV, e.g., and HPV-16, -18, -31, or -33, e.g., a bovine papillomavirus (BPV); inhibiting transformation of a cell by a papillomavirus, e.g., an HPV, e.g., a high-risk HPV, e.g., and HPV-16, -18, -31, or -33, e.g., a bovine papillomavirus; or inhibiting immortalization of a cell, e.g., a human cell, by a papillomavirus, e.g., an HPV, e.g., a high-risk HPV, e.g., and HPV-16, -18, -31, or -33, e.g., a bovine papillomavirus; inhibiting the growth of, or diminishing the size of a wart.

For instance, contacting cells with antisense constructs that alter an E6AP-BP level can inhibit pathological progression of papillomavirus infection, such as preventing or reversing the formation of warts, e.g. Plantar warts (verruca plantaris), common warts (verruca plana), Butcher's common warts, flat warts, genital warts (condyloma acuminatum), or epidermodysplasia verruciformis; as well as treating papillomavirus cells which have become, or are at risk of becoming, transformed and/or immortalized, e.g. cancerous, e.g. a laryngeal papilloma, a focal epithelial, a cervical carcinoma.

In tumor cells, in constrast to p53, elevated or deregulated expression of c-myc is so widespread as to suggest a critical role for myc gene activation in multi-stage carcinomas (Field et all. (1990) *Anticancer Res* 10:1-22; and Spencer et al. (1991) *Adv Cancer Res* 56:1-48). However, such overexpression of myc in these cells is typically believed to be accompanied by expression of other cellular proteins, such as bcl-2. Interestingly, however, almost all tumor cells tested that overexpress myc readily undergo apoptosis in the presence of cytotoxic and growth-inhibitory drugs (Cotter et al. (1990) *Anticancer Res* 10:1153-1159; and Lennon et al. (1990) *Biochem Soc Trans* 18:343-345). Therefore, inhibitors of the ubiquitin-mediated degradation of myc can be used to further deregulate the expression of myc in order to render the cells even more sensitive to a chemotherapeutic treatment, or to possibly upset the careful balance of the transformed cell and cause apoptosis to occur even in the absence of a second cytotoxic drug.

The regulation of cyclin by ubiquitination is yet another therapeutic target which may implicate E6AP-BP inhibitors. Cyclin degradation is a key step governing exit from mitosis and progression into the next cell-cycle. For example, the transition from metaphase to anaphase which marks the end of mitosis in induced by the degradation of cyclin by a ubiquitin-mediated pathway, which in turn leads to the inactivation of cyclin-dependent kinases (cdk) operational at that cycle-cycle stage. As cells enter interphase, cyclin degradation ceases, cyclin accumulates and, as a result of a complex series of post-translational modifications, cyclin /cdk complexes are activated as kinases which drive the cell through mitosis. Cyclin degradation is thus one of the crucial events in exiting mitosis. Indeed, cyclin mutants that retain the ability to activate the cdk complexes, but which cannot be degraded, arrest the cell-cycle in mitosis. Similar cyclin-dependence exists at other points of the cell-cycle as well. Thus, inhibitors of ubiquitin-mediated degradation of a cyclin (such as where the cyclin is chosen from cyclin A, B, C, D1, D2, D3, E, F, G or H) can be used as antiproliferative agents.

Still another candidate substrate for E6AP-BP mediated ubiquitination is the cyclin-dependent kinase inhibitor p27$^{kip1}$ (Polyak et al. (1994) Cell 78:59-66; and Toyoshima et al. (1994) Cell 78:67-74). This protein has been implicated in G$_1$ phase arrest, such as mediated by TGF-β and cell-cell contact. We have found that ubiquitin conjugating enzymes are able to ubiquitinate p27, indicating that cellular turnover of that protein is dependent at least in part on ubiquitin-mediated destruction. Consequently, inhibition of ubiquitin transfer to p27 may result in accumulation of this cell-cycle inhibitor. An agent which inhibits an E6AP-BP mediated degradation of p27 would therefore be a cytostatic agent.

Such cytostatic agents would be useful for inhibiting proliferation of both normal and transformed cells. For example, an inhibitor of ubquitination of p27 could be used to prevent proliferation of lymphocytes, much the same as rapamycin and the like, and could be used as an immunosuppressant. Likewise, accumulation of p27 in fibroblasts could be used as part of a therapy for the treatment of a connective tissue disorder, or for controlling would healing processes.

Modulation of p27 may also be used for the treatment of hyperplastic epidermal conditions, such as psoriasis, as well as for the treatment of neoplastic epidermal conditions such as those characterized by a high proliferization rate for various skin cancers, as for example basal cell carcinoma and squamous cell carcinoma.

Normal cell proliferation is generally marked by responsiveness to negative autocrine or paracrine growth regulators, such as members of the TGF-β family, e.g. TGF-β1, TGF-β2 or TGF-β3, and related polypeptide growth inhibitors, e.g. activins, inhibins, Müllerian inhibiting substance, decapentaplegic, bone morphogenic factors, and vgl (e.g. terminal differentiation inducers). Ordinarily, control of cellular proliferation by such growth regulators, particularly in epithelial and hemopoietic cells, is in the form of growth inhibition with p27 accumulation being associated with at least TGF-β 1 response. This is generally accompanied by differentiation of the cell to a post-mitotic phenotype. However, it has been observed that a significant percentage of human cancers derived from these cells types display a reduced responsiveness to growth regulators such as TGF-β. For instance, some tumors of colorectal, liver epithelial, and epidermal origin show reduced sensitivity and resistance to the growth-inhibitory effects of TGF-β as compared to their normal counterparts. Treatment of such tumors with antagonists of ubiquitination of p27 provides an opportunity to restore the function of a TGF-β mediated checkpoint.

Another aspect of the present invention concerns transgenic animals which are comprised of cells (of that animal) which contain a transgene of the present invention and which preferably (though optionally) express an exogenous E6AP-binding protein in one or more cells in the animal. The E6AP-BP transgene can encode the wild-type form of the protein, or can encode homologs thereof, including both agonists and antagonists, as well as antisense constructs designed to inhibit expression of the endogenous gene. In preferred embodiments, the expression of the transgene is restricted to specific subsets of cells, tissues or developmental stages utilizing, for example, cis-acting sequences that control expression in the desired pattern. In the present invention, such mosaic expression of the subject E6AP-binding proteins can be essential for many forms of lineage analysis and can additionally provide a means to assess the effects of, for example, lack of binding of an E6AP-BP to E6AP, which deficiency might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of a subject E6AP-binding protein. For example, excision of a target sequence which interferes with the expression of a recombinant E6AP-BP gene can be designed to activate expression of that gene. This interference with expression of the protein can result from a variety of mechanisms, such as spatial separation of the gene from a promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al. (1992) PNAS 89:6232-6236; Orban et al. (1992) PNAS 89:6861-6865) or the FLP recombinase system of Saccharomyces cerevisiae (O'Gorman et al. (1991) Science 251:1351-1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) J. Biol. Chem. 259:1509-1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of an E6AP-binding protein can be regulated via regulation of recombinase expression.

Use of the cre/loxP recombinase system to regulate expression of a recombinant E6AP-binding protein, such as cln57 or cln24, requires the construction of a transgenic animal containing transgenes encoding both the Cre recombinase and the subject protein. Animals containing both the Cre recombinase and the recombinant E6AP-BP genes can be provided through the construction of "double" transgenic animals. A convenient method for providing such animals is to mate two transgenic animals each containing a transgene, e.g., the E6AP-BP gene in one animal and recombinase gene in the other.

One advantage derived from initially constructing transgenic animals containing a transgene in a recombinase-mediated expressible format derives from the likelihood that the subject protein will be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues. Thus, the creation of a founder population in which, for example, an antagonistic E6AP-BP transgene is silent will allow the study of, for example, the role of the p53 checkpoint in tissue or at developmental stages which can confer, for example, a lethal phenotype.

Similar conditional transgenes, can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed using, for example, one of the gene therapy constructs described above. By this method, the E6AP-BP transgene could remain silent into adulthood and its expression "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonic target cell. The zygote is the best target for micro-injection. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster et al. (1985) PNAS 82:4438-4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce an E6AP-BP transgene into a non-human animal. The developing non-human embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Van der Putten, supra; Stewart et al. (1987) EMBO J. 6:383-388). Alternatively, infection can be performed at a later stage. Virus or virus-producing cells can be injected into the blastocoele (Jahner et al. (1982) Nature 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonic stem cell (ES). ES cells are obtained from pre-implantation embryos cultured in vitro and fused with embryos (Evans et al. (1981) Nature 292:154-156; Bradley et al. (1984) Nature 309:255-258; Gossler et al. (1986) PNAS 83: 9065-9069; and Robertson et al. (1986) Nature 322:445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468-1474.

Methods of making knock-out or disruption transgenic animals are also generally known. See, for example, *Manipulating the Mouse Embryo*, (Cold Spring Harbor Laboratory Press, Cold Spring Harbor, N.Y., 1986). Recombinase dependent knockouts can also be generated, e.g. by homologous recombination to insert recombinase target sequences, such that tissue specific and/or temporal control of inactivation of a CCR-gene can be controlled as above.

EXEMPLIFICATION

The invention now being generally described, it will be more readily understood by reference to the following examples which are included merely for purposes of illustration of certain aspects and embodiments of the present invention, and are not intended to limit the invention.

Interaction Trap

Manipulation of *E. coli*, yeast and DNA was by standard methods. A general transcription-based selection for protein-protein interactions was used to isolate cDNA encoding proteins able to bind to E6AP. Development of the "interaction trap assay" or ITS, is described in, for example, Gyuris et al. (1993) Cell 75:791-803; Chien et al. (1991) PNAS 88:9578-9582; Dalton et al. (1992) Cell 68:597-612; Durfee et al. (1993) Genes Dev 7:555-569; Vojteck et al. (1993) Cell 74:205-214; Fields et al. (1989) Nature 340:245-246; and U.S. Pat. Ser. No. 5,283,173). As carried out in the present invention, the interaction trap comprises three different components: a fusion protein that contains all or a portion of E6AP and the LexA DNA-binding domain (the "bait"); reporter genes that have no basal transcription and whose transcriptional regulatory sequences are dependent on binding of LexA; and the proteins encoded by an expression library, which are expressed as chimeras and whose amino termini contain an activation domain and other useful moieties (the "fish"). Briefly, baits were produced constitutively from a 2µ HIS3+ plasmid under the control of the ADH1 promoter and contained the LexA carboxy-terminal oligomerization region, which contributes to operator occupancy by LexA derivatives. Baits were made in pLexA(1-202)+PL (described in Ruden et al. *Nature* (1991) 350:250-252; and Gyuris et al. *Cell* (1993) 75:791-803) after PCR amplification of the bait coding sequences from the second amino acid to the Stop codon. PCR primers provided E6AP fragments which could be cloned into pLexA(1-202)+PL as EcoR1-BamH1, EcoR1-Sal1, EcoR1-Xho1 or BamH1-Sal1 fragments. When EcoR1 is used, there are two amino acid inserted (EF) between the last amino acid of LexA and the bait moieties. BamH1 fusion results in five amino acid insertion (EFPGI) between LexA and the fused protein.

Reporters

The LexAop-LEU2 construction replaced the yeast chromosomal LEU2 gene. The other reporter, pRB1840, one of a series of LexAop-GAL1-lacZ genes (Brent et al. (1985) *Cell* 43:729-736; Kamens et al. (1990) *Mol Cell Biol* 10:2840-2847), was carried on a 2µ plasmid. Basal reporter transcription was extremely low, presumably owing both to the removal of the entire upstream activating sequence from both reporters and to the fact that LexA operators introduced into yeast promoters decrease their transcription (Brent and Ptashne (1984) *Nature* 312:612-615). Reporters were chosen to differ in sensitivity. The LEU2 reporter contained three copies of the high affinity LexA-binding site found upstream of *E. coli* colE1, which presumably bind a total of six dimers of the bait. In contrast, the lacZ gene contained a single lower affinity operator that binds a single dimer of the bait. The operators in the LEU2 reporter were closer to the transcription start point than they were in the lacZ reporter. These differences in the number, affinity, and operator position all contribute to that fact that the LEU2 reporter is more sensitive than the lacZ gene.

Expression Vectors and Library

Library proteins were expressed from pJG4-5, a member of a series of expression plasmids designed to be used in the interaction trap and to facilitate analysis of isolated proteins. These plasmids carry the 2µ replicator and the TRP1 marker. pJG4-5, shown in FIG. 1, directs the synthesis of fusion proteins. Proteins expressed from this vector possess the following features: galactose-inducible expression so that their synthesis is conditional, an epitope tag to facilitate detection, a nuclear localization signal to maximize intranuclear concentration to increase selection sensitivity, and an activation domain derived from *E. coli* (Ma and Ptashne (1987) *Cell* 57:113-119), chosen because its activity is not subject to known regulation by yeast proteins and because it is weak enough to avoid toxicity (Gill and Ptashne (1988) *Nature* 334:721-724; Berger et al. (1992) *Cell* 70:251-265) that might restrict the number or type of interacting proteins recovered. EcoRI-XhoI cDNA-containing fragments, which were generated from a quiescent normal fibroblast line (WI38) were introduced into the pJG4-5 plasmid.

Identification of E6AP-Interacting Proteins

We began with yeast cells which contained LexAop-LEU2 and LexAop-lacZ reporters and the LexA-E6AP bait. We introduced the W138 cDNA library (in pJG4-5) into this strain. We recovered 400 transformants on glucose Ura⁻ His⁻ Trp⁻ plates, scraped them, suspended them in approximately 20 ml of 65% glycerol, 10 mM Tris-HCl (pH 7.5), 10 mM MgCl$_2$, and stored the cells in 1 ml aliquots at −80° C. We determined plating efficiency on galactose Ura⁻ His⁻ Trp⁻ after growing 50 µl of cell suspension for 5 hr in 5 ml of YP medium, 2% galactose. For the selection, about 2×10⁷ galactose-viable cells were plated on four standard circular 10 cm galactose Ura⁻ His⁻ Trp⁻ Leu⁻ plates after galactose induction. After 4 days at 30° C., LEU+ colonies appeared and were collected on glucose Ura⁻ His⁻ Trp⁻ master plates and retested on glucose Ura⁻ His⁻ Trp⁻ Leu⁻, galactose Ura⁻ His⁻ Trp⁻ Leu⁻, glucose X-Gal Ura⁻ His⁻ Trp⁻, and galactose X-Gal Ura⁻ His⁻ Trp⁻ plates. Of these, plasmid DNAs were rescued from 100 colonies which showed galactose-dependent growth on Leu⁻ media and galactose-dependent blue color on X-Gal medium (Hoffman and Winston, (1987) *Gene* 57:267-272), introduced into *E. coli* KC8, and transformants collected on Trp-ampicillin plates.

We classified library plasmids by restriction pattern on 1.8% agarose, 0.5× Tris-borate-EDTA gels after digestion with EcoRI and XhoI and either AluI or HaeIII. The cDNA clones, 36 of them, that specifically interacted with E6AP were subjected to DNA sequence analysis. This provides information on the reading frame at the fusion point with the cDNA. In general using this primer we have determined about 200-300 nucleotides of cDNA sequence. In all cases, an open reading frame for the insert has been identified. We are also sequencing with the appropriate primers the 3' end of the cDNA insert.

Subsequently, the pJG4-5 inserts were used to probe full-length cDNA libraries. Full-length clones for 4 of the interactors were obtained and sequenced (see appended sequence listing).

Four candidate proteins were identified based on their apparent ability to interact with E6AP. One of the clones, cln57 shows sequence homology to maternal mRNA from *Xenopus* termed G10. This mRNA is stored in the cytoplasm of stage 6 oocytes until maturation when the process of poly (A) elongation stimulates its translation. Deletion analysis of the 3' untranslated region of G10 RNA has revealed that two sequence elements, UUUUUUAU and AAUAAA were both necessary and sufficient for polyadenylation and polysomal recruitment. It is suggested that progesterone, either in addition to or through MPF/cyclin, induces the synthesis of a factor during very early maturation that stimulates polyadenylation (McGrew and Richter (1990) *EMBO J* 9(11):3743-3751).

Figure 2B:
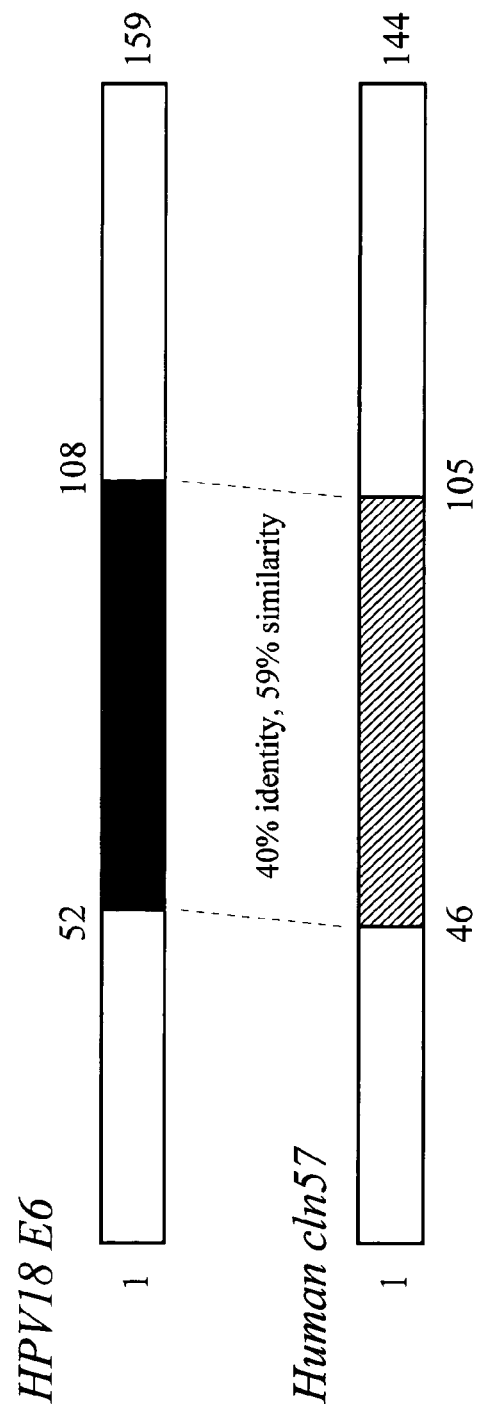
FIG. 2B is a schematic representation of the cln57 and E6 proteins, indicating the relative positioning of the common motif.

Perhaps more interesting was the 50+ stretch of amino acid residues in the cln57 sequence which share 40% identity and 59% similarity to the papillomavirus E6 protein (see FIG. 2A). The implication of this homology, along with the ability of the cln57 protein to bind to E6-AP is strongly suggestive that this novel human protein is a cellular ortholog of the viral E6 protein.

Another clone, cln24, shows homology to sequences on yeast chromosome 8. For example, some similarity was identified between the sequence of cln24 and the open reading frames provided by the complete sequencing of the *S. cerevisiae chromosome VIII cosmid* 9998 (see GenBank accession U00030, locus YSCH9998).

The cln25 clone shared certain sequence homology with aryl sulfotransferase (AST) enzymes. Accordingly, the cln25 gene and gene product are apparent human AST homologs.

Finally, cln42 was identified as a human homolog of the yeast nucleotide excision repair factor, rad23. Other human homologs of this gene have been identified as involved in predisposition to sun (UV) sensitivity and skin cancer. Given the apparent role of E6-AP in control of the cell-cycle checkpoint p53, interaction of E6-AP with other DNA damage machinery of the cell is consistant with its role in cell-cycle regulation.

TABLE 1

| Clone | Nucleotide Sequence | Peptide Sequence | features |
|---|---|---|---|
| clnS7 | SEQ ID No:1 | SEQ ID No:5 | E6 homology |
| cln24 | SEQ ID No:2 | SEQ ID No:6 | homology with a yeast chromosome VIII gene |
| cln25 | SEQ ID No:3 | SEQ ID No:7 | AST homology |
| cln42 | SEQ ID No:4 | SEQ ID No:8 | human rad23 homolog |

All of the above-cited references and publications are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated polypeptide comprising an E6AP-binding polypeptide having the amino acid sequence set forth in SEQ ID No. 5.

2. The polypeptide of claim 1, which modulates at least one of proliferation, differentiation, or survival of a cell which expresses an E6AP protein.

3. The polypeptide of claim 1, which binds to the human E6AP protein.

4. An immunogen comprising the E6AP-binding polypeptide of claim 1, in an immunogenic preparation, said immunogen being capable of eliciting an immune response specific for said E6AP-binding polypeptide.

5. A fusion protein comprising the polypeptide of claim 1, and a second polypeptide sequence.

6. The fusion protein of claim 5, wherein the second polypeptide sequence comprises a label for detecting the presence of said fusion protein or a matrix-binding domain for immobilizing said fusion protein.

7. The fusion protein of claim 6, wherein the second polypeptide sequence has an enzymatic activity.

8. The polypeptide of claim 1, wherein the polypeptide is purified to at least 80% by dry weight.

9. An isolated recombinant E6AP-binding polypeptide encoded by the nucleic acid sequence set forth in SEQ ID No. 1.

10. A fusion protein comprising a first polypeptide sequence which is a DNA binding domain, and a second polypeptide sequence which specifically binds to E6AP, the second polypeptide sequence being encoded by a nucleic acid which hybridizes under high stringency conditions to the nucleic acid sequence set forth in SEQ ID No. 1, wherein the high stringency conditions include a wash step of about 0.2× SSC alt 50° C.

11. A fusion protein comprising a first polypeptide sequence including a transcriptional activation domain, and a second polypeptide sequence which specifically binds to E6AP, the second polypeptide sequence being encoded by a nucleic acid which hybridizes under high stringency conditions to the nucleic acid sequence set forth in SEQ ID NO. 1, wherein the high stringency conditions include a wash step of about 0.2×SSC at 50° C.

12. A reconstituted transcriptional activator protein comprising:
   a. a first fusion protein comprising a first polypeptide sequence which is a DNA binding domain, and a second polypeptide sequence selected from the group consisting of E6AP and an E6AP-binding polypeptide encoded by a nucleic acid which hybridizes under high stringency conditions to the nucleic acid sequence set forth in SEQ ID No. 1, which E6AP-binding polypeptide specifically binds to E6AP, and wherein the high stringency conditions include a wash step of about 0.2×SSC at 50° C.; and
   b. a second fusion protein comprising a first polypeptide sequence which is a transcriptional activation domain, and a second polypeptide sequence which is one of either the E6-AP or E6AP binding polypeptide not provided in the first fusion protein, wherein the second polypeptide sequences of each of the first and second fusion proteins results in formation of a transcriptional activator protein.

13. A purified protein complex consisting essentially of an E6AP polypeptide and an E6AP-binding polypeptide including a naturally occurring amino acid sequence encoded by a gene which hybridizes under high stringency conditions to SEQ ID No. 1, high stringency conditions include a wash step of about 0.2×SSC at 50° C.

14. The protein complex of claim 13, wherein the E6AP-binding polypeptide includes the sequence presented in SEQ ID No. 5.

15. The protein complex of claim 13, wherein the E6AP polypeptide is a human E6AP.

16. The protein complex of claim 13, wherein the protein complex is purified to at least 80% by dry weight.

17. An isolated polypeptide comprising an E6AP-binding polypeptide having an amino acid sequence encoded by a nucleic acid which hybridizes under high stringency conditions to the nucleic acid sequence set forth in SEQ ID No. 1, wherein the high stringency.

* * * * *

UNITED STATES PATENT AND TRADEMARK OFFICE
CERTIFICATE OF CORRECTION

PATENT NO. : 7,566,455 B1
APPLICATION NO. : 08/484878
DATED : July 28, 2009
INVENTOR(S) : Beer-Romero et al.

It is certified that error appears in the above-identified patent and that said Letters Patent is hereby corrected as shown below:

Column 72, line 48, cancel the text beginning with "13. A purified protein complex" to and ending "about 0.2xSSC at 50°C." in column 72, line 53, and insert the following claim:

--13. A purified protein complex consisting essentially of an E6AP polypeptide and an E6AP-binding polypeptide including a naturally occurring amino acid sequence encoded by a gene which hybridizes under high stringency conditions to SEQ ID No. 1, wherein the E6AP polypeptide specifically binds the E6AP-binding polypeptide and the high stringency conditions include a wash step of about 0.2xSSC at 50°C.--

Column 72, line 60, cancel the text beginning with "17. An isolated polypeptide comprising" to and ending "wherein the high stringency." in column 72, line 64, and insert the following claim:

--17. An isolated polypeptide comprising an E6AP-binding polypeptide having an amino acid sequence encoded by a nucleic acid which hybridizes under high stringency conditions to the nucleic acid sequence set forth in SEQ ID No. 1, wherein the high stringency conditions include a wash step of about 0.2xSSC at 50°C.--

Signed and Sealed this

Nineteenth Day of January, 2010

David J. Kappos
*Director of the United States Patent and Trademark Office*

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 435 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..432

(xi) SEQUENCE DESCRIPTION: SEQ ID NO: 1:

```
ATG CCT AAA GTC AAA AGA AGC CGG AAA GCA CCC CCA GAT GGC TGG GAG         48
Met Pro Lys Val Lys Arg Ser Arg Lys Ala Pro Pro Asp Gly Trp Glu
 1               5                  10                  15

TTG ATT GAG CCA ACA CTG GAT GAA TTA GAT CAA AAG ATG AGA GAA GCT         96
Leu Ile Glu Pro Thr Leu Asp Glu Leu Asp Gln Lys Met Arg Glu Ala
                20                  25                  30

GAA ACA GAA CCG CAT GAG GGA AAG AGG AAA GTG GAA TCT CTG TGG CCC        144
Glu Thr Glu Pro His Glu Gly Lys Arg Lys Val Glu Ser Leu Trp Pro
            35                  40                  45

ATC TTC AGG ATC CAC CAC CAG AAA ACC CGC TAC ATC TTC GAC CTC TTT        192
Ile Phe Arg Ile His His Gln Lys Thr Arg Tyr Ile Phe Asp Leu Phe
        50                  55                  60

TAC AAG CGG AAA GCC ATC AGC AGA GAA CTC TAT GAA TAT TGT ATT AAA        240
Tyr Lys Arg Lys Ala Ile Ser Arg Glu Leu Tyr Glu Tyr Cys Ile Lys
 65                  70                  75                  80

GAA GGC TAT GCA GAC AAA AAC CTG ATT GCA AAA TGG AAA AAG CAA GGA        288
Glu Gly Tyr Ala Asp Lys Asn Leu Ile Ala Lys Trp Lys Lys Gln Gly
                85                  90                  95

TAT GAG AAC TTG TGC TGC CTG CGG TGC ATT CAG ACA CGG GAC ACC AAC        336
Tyr Glu Asn Leu Cys Cys Leu Arg Cys Ile Gln Thr Arg Asp Thr Asn
            100                 105                 110

TTC GGG ACG AAC TGC ATC TGC CGC GTG CCC AAA AGC AAG CTG GAA GTG        384
Phe Gly Thr Asn Cys Ile Cys Arg Val Pro Lys Ser Lys Leu Glu Val
        115                 120                 125

GGC CGC ATC ATC GAG TGC ACA CAC TGT GGC TGT CGT GGC TGC TCT GGC        432
Gly Arg Ile Ile Glu Cys Thr His Cys Gly Cys Arg Gly Cys Ser Gly
    130                 135                 140

TGA                                                                    435
```

(2) INFORMATION FOR SEQ ID NO: 2:

(i) SEQUENCE CHARACTERISTICS:
        (A) LENGTH: 1116 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1113

(xi) SEQUENCE DESCRIPTION: SEQ ID NO: 2:

```
ATG GTG TGT GTG GAC AAC AGT GAG TAT ATG CGG AAT GGA GAC TTC TTA        48
Met Val Cys Val Asp Asn Ser Glu Tyr Met Arg Asn Gly Asp Phe Leu
  1               5                  10                  15

CCC ACC AGG CTG CAG GCC CAG CAG GAT GCT GTC AAC ATA GTT TGT CAT        96
Pro Thr Arg Leu Gln Ala Gln Gln Asp Ala Val Asn Ile Val Cys His
             20                  25                  30

TCA AAG ACC CGC AGC AAC CCT GAG AAC AAC GTG GGC CTT ATC ACA CTG       144
Ser Lys Thr Arg Ser Asn Pro Glu Asn Asn Val Gly Leu Ile Thr Leu
         35                  40                  45

GCT AAT GAC TGT GAA GTG CTG ACC ACA CTC ACC CCA GAC ACT GGC CGT       192
Ala Asn Asp Cys Glu Val Leu Thr Thr Leu Thr Pro Asp Thr Gly Arg
 50                  55                  60

ATC CTG TCC AAG CTA CAT ACT GTC CAA CCC AAG GGC AAG ATC ACC TTC       240
Ile Leu Ser Lys Leu His Thr Val Gln Pro Lys Gly Lys Ile Thr Phe
 65                  70                  75                  80

TGC ACG GGC ATC CGC GTG GCC CAT CTG GCT CTG AAG CAC CGA CAA GGC       288
Cys Thr Gly Ile Arg Val Ala His Leu Ala Leu Lys His Arg Gln Gly
             85                  90                  95

AAG AAT CAC AAG ATG CGC ATC ATT GCC TTT GTG GGA AGC CCA GTG GAG       336
Lys Asn His Lys Met Arg Ile Ile Ala Phe Val Gly Ser Pro Val Glu
            100                 105                 110

GAC AAT GAG AAG GAT CTG GTG AAA CTG GCT AAA CGC CTC AAG AAG GAG       384
Asp Asn Glu Lys Asp Leu Val Lys Leu Ala Lys Arg Leu Lys Lys Glu
        115                 120                 125

AAA GTA AAT GTT GAC ATT ATC AAT TTT GGG GAA GAG GAG GTG AAC ACA       432
Lys Val Asn Val Asp Ile Ile Asn Phe Gly Glu Glu Glu Val Asn Thr
130                 135                 140

GAA AAG CTG ACA GCC TTT GTA AAC ACG TTG AAT GGC AAA GAT GGA ACC       480
Glu Lys Leu Thr Ala Phe Val Asn Thr Leu Asn Gly Lys Asp Gly Thr
145                 150                 155                 160

GGT TCT CAT CTG GTG ACA GTG CCT CCT GGG CCC AGT TTG GCT GAT GCT       528
Gly Ser His Leu Val Thr Val Pro Pro Gly Pro Ser Leu Ala Asp Ala
                165                 170                 175

CTC ATC AGT TCT CCG ATT TTG GCT GGT GAA GGT GGT GCC ATG CTG GGT       576
Leu Ile Ser Ser Pro Ile Leu Ala Gly Glu Gly Gly Ala Met Leu Gly
            180                 185                 190

CTT GGT GCC AGT GAC TTT GAA TTT GGA GTA GAT CCC AGT GCT GAT CCT       624
Leu Gly Ala Ser Asp Phe Glu Phe Gly Val Asp Pro Ser Ala Asp Pro
        195                 200                 205

GAG CTG GCC TTG GCC CTT CGT GTA TCT ATG GAA GAG CAG CGG CAG CGG       672
Glu Leu Ala Leu Ala Leu Arg Val Ser Met Glu Glu Gln Arg Gln Arg
    210                 215                 220

CAG GAG GAG GAG GCC CGG CGG GCA GCT GCA GCT TCT GCT GCT GAG GCC       720
Gln Glu Glu Glu Ala Arg Arg Ala Ala Ala Ala Ser Ala Ala Glu Ala
225                 230                 235                 240

GGG ATT GCT ACG ACT GGG ACT GAA GAC TCA GAC GAT GCC CTG CTG AAG       768
```

-continued

```
Gly Ile Ala Thr Thr Gly Thr Glu Asp Ser Asp Asp Ala Leu Leu Lys
                245                 250                 255

ATG ACC ATC AGC CAG CAA GAG TTT GGC CGC ACT GGG CTT CCT GAC CTA         816
Met Thr Ile Ser Gln Gln Glu Phe Gly Arg Thr Gly Leu Pro Asp Leu
        260                 265                 270

AGC AGT ATG ACT GAG GAA GAG CAG ATT GCT TAT GCC ATG CAG ATG TCC         864
Ser Ser Met Thr Glu Glu Glu Gln Ile Ala Tyr Ala Met Gln Met Ser
            275                 280                 285

CTG CAG GGA GCA GAG TTT GGC CAG GCG GAA TCA GCA GAC ATT GAT GCC         912
Leu Gln Gly Ala Glu Phe Gly Gln Ala Glu Ser Ala Asp Ile Asp Ala
        290                 295                 300

AGC TCA GCT ATG GAC ACA TCC GAG CCA GCC AAG GAG GAG GAT GAT TAC         960
Ser Ser Ala Met Asp Thr Ser Glu Pro Ala Lys Glu Glu Asp Asp Tyr
305                 310                 315                 320

GAC GTG ATG CAG GAC CCC GAG TTC CTT CAG AGT GTC CTA GAG AAC CTC        1008
Asp Val Met Gln Asp Pro Glu Phe Leu Gln Ser Val Leu Glu Asn Leu
                325                 330                 335

CCA GGT GTG GAT CCC AAC AAT GAA GCC ATT CGA AAT GCT ATG GGC TCC        1056
Pro Gly Val Asp Pro Asn Asn Glu Ala Ile Arg Asn Ala Met Gly Ser
            340                 345                 350

CTG GCC TCC CAG GCC ACC AAG GAC GGC AAG AAG GAC AAG AAG GAG GAA        1104
Leu Ala Ser Gln Ala Thr Lys Asp Gly Lys Lys Asp Lys Lys Glu Glu
        355                 360                 365

GAC AAG AAG TGA                                                        1116
Asp Lys Lys
    370

(2) INFORMATION FOR SEQ ID NO: 3:

(i) SEQUENCE CHARACTERISTICS:
        (A) LENGTH: 888 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..885

(xi) SEQUENCE DESCRIPTION: SEQ ID NO: 3:

ATG GAG CTG ATC CAG GAC ACC TCC CGC CCG CCA CTG GAG TAC GTG AAG          48
Met Glu Leu Ile Gln Asp Thr Ser Arg Pro Pro Leu Glu Tyr Val Lys
  1               5                  10                  15

GGG GTC CCG CTC ATC AAG TAC TTT GCA GAG GCA CTG GGG CCC CTG CAG          96
Gly Val Pro Leu Ile Lys Tyr Phe Ala Glu Ala Leu Gly Pro Leu Gln
                20                  25                  30

AGC TTC CAA GCC CGA CCT GAT GAC CTG CTC ATC AAC ACC TAC CCC AAG         144
Ser Phe Gln Ala Arg Pro Asp Asp Leu Leu Ile Asn Thr Tyr Pro Lys
            35                  40                  45

TCT GGC ACC ACC TGG GTG AGC CAG ATA CTG GAC ATG ATC TAC CAG GGC         192
Ser Gly Thr Thr Trp Val Ser Gln Ile Leu Asp Met Ile Tyr Gln Gly
        50                  55                  60

GGC GAC CTA GAG AAG TGT AAC CGG GCT CCC ATC TAC GTA CGG GTG CCC         240
Gly Asp Leu Glu Lys Cys Asn Arg Ala Pro Ile Tyr Val Arg Val Pro
 65                  70                  75                  80

TTC CTT GAG GTC AAT GAT CCA GGG GAA CCC TCA GGG CTG GAG ACT CTG         288
Phe Leu Glu Val Asn Asp Pro Gly Glu Pro Ser Gly Leu Glu Thr Leu
                85                  90                  95

AAA GAC ACA CCG CCC CCA CGG CTC ATC AAG TCA CAC CTG CCC CTG GCT         336
Lys Asp Thr Pro Pro Pro Arg Leu Ile Lys Ser His Leu Pro Leu Ala
            100                 105                 110
```

-continued

```
CTG CTC CCT CAG ACT CTG TTG GAT CAG AAG GTC AAG GTG GTC TAT GTT         384
Leu Leu Pro Gln Thr Leu Leu Asp Gln Lys Val Lys Val Val Tyr Val
        115                 120                 125

GCC CGA AAC CCA AAG GAC GTG GCG GTC TCC TAC TAC CAT TTC CAC CGT         432
Ala Arg Asn Pro Lys Asp Val Ala Val Ser Tyr Tyr His Phe His Arg
        130                 135                 140

ATG GAA AAG GCG CAC CCT GAG CCT GGG ACC TGG GAC AGC TTC CTG GAA         480
Met Glu Lys Ala His Pro Glu Pro Gly Thr Trp Asp Ser Phe Leu Glu
145                 150                 155                 160

AAG TTC ATG GCT GGA GAA GTG TCC TAC GGG TCC TGG TAC CAG CAC GTG         528
Lys Phe Met Ala Gly Glu Val Ser Tyr Gly Ser Trp Tyr Gln His Val
                165                 170                 175

CAG GAG TGG TGG GAG CTG AGC CGC ACC CAC CCT GTT CTC TAC CTC TTC         576
Gln Glu Trp Trp Glu Leu Ser Arg Thr His Pro Val Leu Tyr Leu Phe
            180                 185                 190

TAT GAA GAC ATG AAG GAG AAC CCC AAA AGG GAG ATT CAA AAG ATC CTG         624
Tyr Glu Asp Met Lys Glu Asn Pro Lys Arg Glu Ile Gln Lys Ile Leu
        195                 200                 205

GAG TTT GTG GGG CGC TCC CTG CCA GAG GAG ACC ATG GAC TTC ATG GTT         672
Glu Phe Val Gly Arg Ser Leu Pro Glu Glu Thr Met Asp Phe Met Val
210                 215                 220

CAG CAC ACG TCG TTC AAG GAG ATG AAG AAG AAC CCT ATG ACC AAC TAC         720
Gln His Thr Ser Phe Lys Glu Met Lys Lys Asn Pro Met Thr Asn Tyr
225                 230                 235                 240

ACC ACC GTC CCC CAG GAG CTC ATG GAC CAC AGC ATC TCC CCC TTC ATG         768
Thr Thr Val Pro Gln Glu Leu Met Asp His Ser Ile Ser Pro Phe Met
                245                 250                 255

AGG AAA GGC ATG GCT GGG GAC TGG AAG ACC ACC TTC ACC GTG GCG CAG         816
Arg Lys Gly Met Ala Gly Asp Trp Lys Thr Thr Phe Thr Val Ala Gln
            260                 265                 270

AAT GAG CGC TTC GAT GCG GAC TAT GCG GAG AAG ATG GCA GGC TGC AGC         864
Asn Glu Arg Phe Asp Ala Asp Tyr Ala Glu Lys Met Ala Gly Cys Ser
        275                 280                 285

CTC AGC TTC CGC TCT GAG CTG TGA                                         888
Leu Ser Phe Arg Ser Glu Leu
        290                 295

(2) INFORMATION FOR SEQ ID NO: 4:

(i) SEQUENCE CHARACTERISTICS:
        (A) LENGTH: 1092 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1089

(xi) SEQUENCE DESCRIPTION: SEQ ID NO: 4:

ATG GCC GTC ACC ATC ACG CTC AAA ACG CTG CAG CAG CAG ACC TTC AAG          48
Met Ala Val Thr Ile Thr Leu Lys Thr Leu Gln Gln Gln Thr Phe Lys
1               5                   10                  15

ATC CGC ATG GAG CCT GAC GAG ACG GTG AAG GTG CTA AAG GAG AAG ATA          96
Ile Arg Met Glu Pro Asp Glu Thr Val Lys Val Leu Lys Glu Lys Ile
                20                  25                  30

GAA GCT GAG AAG GGT CGT GAT GCC TTC CCC GTG GCT GGA CAG AAA CTC         144
Glu Ala Glu Lys Gly Arg Asp Ala Phe Pro Val Ala Gly Gln Lys Leu
            35                  40                  45

ATC TAT GCC GGC AAG ATC TTG AGT GAC GAT GTC CCT ATC AGG GAC TAT         192
```

```
               Ile Tyr Ala Gly Lys Ile Leu Ser Asp Asp Val Pro Ile Arg Asp Tyr
                    50                  55                  60

CGC ATC GAT GAG AAG AAC TTT GTG GTC GTC ATG GTG ACC AAG ACC AAA          240
Arg Ile Asp Glu Lys Asn Phe Val Val Val Met Val Thr Lys Thr Lys
 65                  70                  75                  80

GCC GGC CAG GGT ACC TCA GCA CCC CCA GAG GCC TCA CCC ACA GCT GCC          288
Ala Gly Gln Gly Thr Ser Ala Pro Pro Glu Ala Ser Pro Thr Ala Ala
                     85                  90                  95

CCA GAG TCC TCT ACA TCC TTC CCG CCT GCC CCC ACC TCA GGC ATG TCC          336
Pro Glu Ser Ser Thr Ser Phe Pro Pro Ala Pro Thr Ser Gly Met Ser
                100                 105                 110

CAT CCC CCA CCT GCC GCC AGA GAG GAC AAG AGC CCA TCA GAG GAA TCC          384
His Pro Pro Pro Ala Ala Arg Glu Asp Lys Ser Pro Ser Glu Glu Ser
                115                 120                 125

GCC CCC ACG ACG TCC CCA GAG TCT GTG TCA GGC TCT GTT CCC TCT TCA          432
Ala Pro Thr Thr Ser Pro Glu Ser Val Ser Gly Ser Val Pro Ser Ser
                130                 135                 140

GGT AGC AGC GGG CGA GAG GAA GAC GCG GCC TCC ACG CTA GTG ACG GGC          480
Gly Ser Ser Gly Arg Glu Glu Asp Ala Ala Ser Thr Leu Val Thr Gly
145                 150                 155                 160

TCT GAG TAT GAG ACG ATG CTG ACG GAG ATC ATG TCC ATG GGC TAT GAG          528
Ser Glu Tyr Glu Thr Met Leu Thr Glu Ile Met Ser Met Gly Tyr Glu
                165                 170                 175

CGA GAG CGG GTC GTG GCC GCC CTG AGA GCC AGC TAC AAC AAC CCC CAC          576
Arg Glu Arg Val Val Ala Ala Leu Arg Ala Ser Tyr Asn Asn Pro His
                180                 185                 190

CGA GCC GTG GAG TAT CTG CTC ACG GGA ATT CCT GGG AGC CCC GAG CCG          624
Arg Ala Val Glu Tyr Leu Leu Thr Gly Ile Pro Gly Ser Pro Glu Pro
                195                 200                 205

GAA CAC GGT TCT GTC CAG GAG AGC CAG GTA TCG GAG CAG CCG GCC ACG          672
Glu His Gly Ser Val Gln Glu Ser Gln Val Ser Glu Gln Pro Ala Thr
210                 215                 220

GAA GCA GCA GGA GAG AAC CCC CTG GAG TTC CTG CGG GAC CAG CCC CAG          720
Glu Ala Ala Gly Glu Asn Pro Leu Glu Phe Leu Arg Asp Gln Pro Gln
225                 230                 235                 240

TTC CAG AAC ATG CGG CAG GTG ATT CAG CAG AAC CCT GCG CTG CTG CCC          768
Phe Gln Asn Met Arg Gln Val Ile Gln Gln Asn Pro Ala Leu Leu Pro
                245                 250                 255

GCC CTG CTC CAG CAG CTG GGC CAG GAG AAC CCT CAG CTT TTA CAG CAA          816
Ala Leu Leu Gln Gln Leu Gly Gln Glu Asn Pro Gln Leu Leu Gln Gln
                260                 265                 270

ATC AGC CGG CAC CAG GAG CAG TTC ATC CAG ATG CTG AAC GAG CCC CCT          864
Ile Ser Arg His Gln Glu Gln Phe Ile Gln Met Leu Asn Glu Pro Pro
                275                 280                 285

GGG GAG CTG GCG GAC ATC TCA GAT GTG GAG GGG GAG GTG GGC GCC ATA          912
Gly Glu Leu Ala Asp Ile Ser Asp Val Glu Gly Glu Val Gly Ala Ile
                290                 295                 300

GGA GAG GAG GCC CCG CAG ATG AAC TAC ATC CAG GTG ACG CCG CAG GAG          960
Gly Glu Glu Ala Pro Gln Met Asn Tyr Ile Gln Val Thr Pro Gln Glu
305                 310                 315                 320

AAA GAA GCT ATA GAG AGG TTG AAG GCC CTG GGC TTC CCA GAG AGC CTG         1008
Lys Glu Ala Ile Glu Arg Leu Lys Ala Leu Gly Phe Pro Glu Ser Leu
                325                 330                 335

GTC ATC CAG GCC TAT TTC GCG TGT GAA AAA AAT GAG AAC TTG GCT GCC         1056
Val Ile Gln Ala Tyr Phe Ala Cys Glu Lys Asn Glu Asn Leu Ala Ala
                340                 345                 350

AAC TTC CTC CTG AGT CAG AAC TTT GAT GAC GAG TGA                         1092
Asn Phe Leu Leu Ser Gln Asn Phe Asp Asp Glu
                355                 360
```

(2) INFORMATION FOR SEQ ID NO: 5:

(i) SEQUENCE CHARACTERISTICS:
        (A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Pro Lys Val Lys Arg Ser Arg Lys Ala Pro Pro Asp Gly Trp Glu
 1               5                  10                  15

Leu Ile Glu Pro Thr Leu Asp Glu Leu Asp Gln Lys Met Arg Glu Ala
             20                  25                  30

Glu Thr Glu Pro His Glu Gly Lys Arg Lys Val Glu Ser Leu Trp Pro
         35                  40                  45

Ile Phe Arg Ile His His Gln Lys Thr Arg Tyr Ile Phe Asp Leu Phe
     50                  55                  60

Tyr Lys Arg Lys Ala Ile Ser Arg Glu Leu Tyr Glu Tyr Cys Ile Lys
 65                  70                  75                  80

Glu Gly Tyr Ala Asp Lys Asn Leu Ile Ala Lys Trp Lys Lys Gln Gly
                 85                  90                  95

Tyr Glu Asn Leu Cys Cys Leu Arg Cys Ile Gln Thr Arg Asp Thr Asn
                100                 105                 110

Phe Gly Thr Asn Cys Ile Cys Arg Val Pro Lys Ser Lys Leu Glu Val
            115                 120                 125

Gly Arg Ile Ile Glu Cys Thr His Cys Gly Cys Arg Gly Cys Ser Gly
        130                 135                 140
```

(2) INFORMATION FOR SEQ ID NO: 6:

(i) SEQUENCE CHARACTERISTICS:
        (A) LENGTH: 371 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Val Cys Val Asp Asn Ser Glu Tyr Met Arg Asn Gly Asp Phe Leu
 1               5                  10                  15

Pro Thr Arg Leu Gln Ala Gln Gln Asp Ala Val Asn Ile Val Cys His
             20                  25                  30

Ser Lys Thr Arg Ser Asn Pro Glu Asn Asn Val Gly Leu Ile Thr Leu
         35                  40                  45

Ala Asn Asp Cys Glu Val Leu Thr Thr Leu Thr Pro Asp Thr Gly Arg
     50                  55                  60

Ile Leu Ser Lys Leu His Thr Val Gln Pro Lys Gly Lys Ile Thr Phe
 65                  70                  75                  80

Cys Thr Gly Ile Arg Val Ala His Leu Ala Leu Lys His Arg Gln Gly
                 85                  90                  95

Lys Asn His Lys Met Arg Ile Ile Ala Phe Val Gly Ser Pro Val Glu
                100                 105                 110

Asp Asn Glu Lys Asp Leu Val Lys Leu Ala Lys Arg Leu Lys Lys Glu
            115                 120                 125

Lys Val Asn Val Asp Ile Ile Asn Phe Gly Glu Glu Glu Val Asn Thr
        130                 135                 140

Glu Lys Leu Thr Ala Phe Val Asn Thr Leu Asn Gly Lys Asp Gly Thr
```

-continued

```
                145                 150                 155                 160
Gly Ser His Leu Val Thr Val Pro Pro Gly Pro Ser Leu Ala Asp Ala
                165                 170                 175
Leu Ile Ser Ser Pro Ile Leu Ala Gly Glu Gly Ala Met Leu Gly
                180                 185                 190
Leu Gly Ala Ser Asp Phe Glu Phe Gly Val Asp Pro Ser Ala Asp Pro
                195                 200                 205
Glu Leu Ala Leu Ala Leu Arg Val Ser Met Glu Glu Gln Arg Gln Arg
                210                 215                 220
Gln Glu Glu Glu Ala Arg Arg Ala Ala Ala Ser Ala Ala Glu Ala
225                 230                 235                 240
Gly Ile Ala Thr Thr Gly Thr Glu Asp Ser Asp Asp Ala Leu Leu Lys
                245                 250                 255
Met Thr Ile Ser Gln Gln Glu Phe Gly Arg Thr Gly Leu Pro Asp Leu
                260                 265                 270
Ser Ser Met Thr Glu Glu Glu Gln Ile Ala Tyr Ala Met Gln Met Ser
                275                 280                 285
Leu Gln Gly Ala Glu Phe Gly Gln Ala Glu Ser Ala Asp Ile Asp Ala
                290                 295                 300
Ser Ser Ala Met Asp Thr Ser Glu Pro Ala Lys Glu Glu Asp Asp Tyr
305                 310                 315                 320
Asp Val Met Gln Asp Pro Glu Phe Leu Gln Ser Val Leu Glu Asn Leu
                325                 330                 335
Pro Gly Val Asp Pro Asn Asn Glu Ala Ile Arg Asn Ala Met Gly Ser
                340                 345                 350
Leu Ala Ser Gln Ala Thr Lys Asp Gly Lys Lys Asp Lys Lys Glu Glu
                355                 360                 365
Asp Lys Lys
370

(2) INFORMATION FOR SEQ ID NO: 7:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION: SEQ ID NO: 7:

Met Glu Leu Ile Gln Asp Thr Ser Arg Pro Pro Leu Glu Tyr Val Lys
1               5                   10                  15
Gly Val Pro Leu Ile Lys Tyr Phe Ala Glu Ala Leu Gly Pro Leu Gln
                20                  25                  30
Ser Phe Gln Ala Arg Pro Asp Asp Leu Leu Ile Asn Thr Tyr Pro Lys
                35                  40                  45
Ser Gly Thr Thr Trp Val Ser Gln Ile Leu Asp Met Ile Tyr Gln Gly
                50                  55                  60
Gly Asp Leu Glu Lys Cys Asn Arg Ala Pro Ile Tyr Val Arg Val Pro
65                  70                  75                  80
Phe Leu Glu Val Asn Asp Pro Gly Glu Pro Ser Gly Leu Glu Thr Leu
                85                  90                  95
Lys Asp Thr Pro Pro Arg Leu Ile Lys Ser His Leu Pro Leu Ala
                100                 105                 110
Leu Leu Pro Gln Thr Leu Leu Asp Gln Lys Val Lys Val Val Tyr Val
                115                 120                 125
```

```
Ala Arg Asn Pro Lys Asp Val Ala Val Ser Tyr Tyr His Phe His Arg
        130                 135                 140
Met Glu Lys Ala His Pro Glu Pro Gly Thr Trp Asp Ser Phe Leu Glu
145                 150                 155                 160
Lys Phe Met Ala Gly Glu Val Ser Tyr Gly Ser Trp Tyr Gln His Val
                165                 170                 175
Gln Glu Trp Trp Glu Leu Ser Arg Thr His Pro Val Leu Tyr Leu Phe
                180                 185                 190
Tyr Glu Asp Met Lys Glu Asn Pro Lys Arg Glu Ile Gln Lys Ile Leu
            195                 200                 205
Glu Phe Val Gly Arg Ser Leu Pro Glu Glu Thr Met Asp Phe Met Val
        210                 215                 220
Gln His Thr Ser Phe Lys Glu Met Lys Lys Asn Pro Met Thr Asn Tyr
225                 230                 235                 240
Thr Thr Val Pro Gln Glu Leu Met Asp His Ser Ile Ser Pro Phe Met
                245                 250                 255
Arg Lys Gly Met Ala Gly Asp Trp Lys Thr Thr Phe Thr Val Ala Gln
                260                 265                 270
Asn Glu Arg Phe Asp Ala Asp Tyr Ala Glu Lys Met Ala Gly Cys Ser
            275                 280                 285
Leu Ser Phe Arg Ser Glu Leu
        290                 295

(2) INFORMATION FOR SEQ ID NO: 8:

(i) SEQUENCE CHARACTERISTICS:
        (A) LENGTH: 363 amino acids
        (B) TYPE: amino acid
        (D) TOPOLOGY: linear (ii) MOLECULE TYPE: protein (xi) SEQUENCE DESCRIPTION: SEQ ID NO: 8:

Met Ala Val Thr Ile Thr Leu Lys Thr Leu Gln Gln Gln Thr Phe Lys
1               5                   10                  15
Ile Arg Met Glu Pro Asp Glu Thr Val Lys Val Leu Lys Glu Lys Ile
                20                  25                  30
Glu Ala Glu Lys Gly Arg Asp Ala Phe Pro Val Ala Gly Gln Lys Leu
            35                  40                  45
Ile Tyr Ala Gly Lys Ile Leu Ser Asp Asp Val Pro Ile Arg Asp Tyr
        50                  55                  60
Arg Ile Asp Glu Lys Asn Phe Val Val Met Val Thr Lys Thr Lys
65                  70                  75                  80
Ala Gly Gln Gly Thr Ser Ala Pro Pro Glu Ala Ser Pro Thr Ala Ala
                85                  90                  95
Pro Glu Ser Ser Thr Ser Phe Pro Pro Ala Pro Thr Ser Gly Met Ser
                100                 105                 110
His Pro Pro Pro Ala Ala Arg Glu Asp Lys Ser Pro Ser Glu Glu Ser
            115                 120                 125
Ala Pro Thr Thr Ser Pro Glu Ser Val Ser Gly Ser Val Pro Ser Ser
        130                 135                 140
Gly Ser Ser Gly Arg Glu Glu Asp Ala Ala Ser Thr Leu Val Thr Gly
145                 150                 155                 160
Ser Glu Tyr Glu Thr Met Leu Thr Glu Ile Met Ser Met Gly Tyr Glu
                165                 170                 175
```

-continued

```
Arg Glu Arg Val Val Ala Ala Leu Arg Ala Ser Tyr Asn Asn Pro His
            180                 185                 190

Arg Ala Val Glu Tyr Leu Leu Thr Gly Ile Pro Gly Ser Pro Glu Pro
            195                 200                 205

Glu His Gly Ser Val Gln Glu Ser Gln Val Ser Glu Gln Pro Ala Thr
            210                 215                 220

Glu Ala Ala Gly Glu Asn Pro Leu Glu Phe Leu Arg Asp Gln Pro Gln
225                 230                 235                 240

Phe Gln Asn Met Arg Gln Val Ile Gln Asn Pro Ala Leu Leu Pro
                245                 250                 255

Ala Leu Leu Gln Gln Leu Gly Gln Glu Asn Pro Gln Leu Leu Gln Gln
            260                 265                 270

Ile Ser Arg His Gln Glu Gln Phe Ile Gln Met Leu Asn Glu Pro Pro
            275                 280                 285

Gly Glu Leu Ala Asp Ile Ser Asp Val Glu Gly Glu Val Gly Ala Ile
            290                 295                 300

Gly Glu Glu Ala Pro Gln Met Asn Tyr Ile Gln Val Thr Pro Gln Glu
305                 310                 315                 320

Lys Glu Ala Ile Glu Arg Leu Lys Ala Leu Gly Phe Pro Glu Ser Leu
                325                 330                 335

Val Ile Gln Ala Tyr Phe Ala Cys Glu Lys Asn Glu Asn Leu Ala Ala
            340                 345                 350

Asn Phe Leu Leu Ser Gln Asn Phe Asp Asp Glu
            355                 360
```

(2) INFORMATION FOR SEQ ID NO: 9:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 9:

```
Pro Pro Lys Lys Lys Arg Lys Val Ala
1               5
```

(2) INFORMATION FOR SEQ ID NO: 10:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 10:

```
Tyr Pro Tyr Asp Val Pro Asp Tyr Ala
1               5
```

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear

```
        (ii) MOLECULE TYPE: cDNA (xi) SEQUENCE DESCRIPTION: SEQ ID NO: 11:

TACCAGCCTC TTGCTGAGTG GAGA                                              24

(2) INFORMATION FOR SEQ ID NO: 12:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 12:

TAGACAAGCC GACAACCTTG ATTG                                              24

(2) INFORMATION FOR SEQ ID NO: 13:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 13:

GAATTCTGCG GCCGC                                                        15

(2) INFORMATION FOR SEQ ID NO: 14:

(i) SEQUENCE CHARACTERISTICS:
            (A) LENGTH: 345 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 7..327

(xi) SEQUENCE DESCRIPTION: SEQ ID NO: 14:

AAGCTT ATG GGT GCT CCT CCA AAA AAG AAG AGA AAG GTA GCT GGT ATC          48
       Met Gly Ala Pro Pro Lys Lys Lys Arg Lys Val Ala Gly Ile
         1               5                  10

AAT AAA GAT ATC GAG GAG TGC AAT GCC ATC ATT GAG CAG TTT ATC GAC         96
Asn Lys Asp Ile Glu Glu Cys Asn Ala Ile Ile Glu Gln Phe Ile Asp
 15                  20                  25                  30

TAC CTG CGC ACC GGA CAG GAG ATG CCG ATG GAA ATG GCG GAT CAG GCG        144
Tyr Leu Arg Thr Gly Gln Glu Met Pro Met Glu Met Ala Asp Gln Ala
                 35                  40                  45

ATT AAC GTG GTG CCG GGC ATG ACG CCG AAA ACC ATT CTT CAC GCC GGG        192
Ile Asn Val Val Pro Gly Met Thr Pro Lys Thr Ile Leu His Ala Gly
                 50                  55                  60

CCG CCG ATC CAG CCT GAC TGG CTG AAA TCG AAT GGT TTT CAT GAA ATT        240
Pro Pro Ile Gln Pro Asp Trp Leu Lys Ser Asn Gly Phe His Glu Ile
                 65                  70                  75

GAA GCG GAT GTT AAC GAT ACC AGC CTC TTG CTG AGT GGA GAT GCC TCC        288
Glu Ala Asp Val Asn Asp Thr Ser Leu Leu Leu Ser Gly Asp Ala Ser
     80                  85                  90

TAC CCT TAT GAT GTG CCA GAT TAT GCC TCT CCC GAA TTC GGCCGACTCG         337
Tyr Pro Tyr Asp Val Pro Asp Tyr Ala Ser Pro Glu Phe
```

```
                        95                  100                 105
AGAAGCTT                                                                            345

(2) INFORMATION FOR SEQ ID NO: 15:

(i) SEQUENCE CHARACTERISTICS:
        (A) LENGTH: 57 amino acids
        (B) TYPE: amino acid
        (D) TOPOLOGY: linear (ii) MOLECULE TYPE: protein (xi) SEQUENCE DESCRIPTION: SEQ ID NO: 15:

Leu Phe Val Val Tyr Arg Asp Ser Ile Phe His Ala Ala Cys His Lys
  1           5                  10                 15

Cys Ile Asp Phe Tyr Ser Arg Ile Arg Glu Leu Arg His Tyr Ser Asp
           20                  25                 30

Ser Val Tyr Gly Asp Thr Leu Glu Lys Leu Thr Asn Thr Gly Leu Tyr
           35                  40                 45

Asn Leu Leu Ile Arg Cys Leu Arg Cys
         50                 55
```